(12) United States Patent
Falkenburg et al.

(10) Patent No.: US 11,263,883 B2
(45) Date of Patent: Mar. 1, 2022

(54) SYSTEM-ON-CHIP FOR SMOKE ALARM

(71) Applicant: Texas Instruments Incorporated, Dallas, TX (US)

(72) Inventors: Grant Evan Falkenburg, Dallas, TX (US); Shinya Morita, Plano, TX (US); Mehedi Hassan, Plano, TX (US); Lundy Findlay Taylor, Plano, TX (US)

(73) Assignee: Texas Instruments Incorporated, Dallas, TX (US)

( * ) Notice: Subject to any disclaimer, the term of this patent is extended or adjusted under 35 U.S.C. 154(b) by 0 days.

(21) Appl. No.: 16/850,237

(22) Filed: Apr. 16, 2020

(65) Prior Publication Data
US 2021/0327239 A1   Oct. 21, 2021

(51) Int. Cl.
| G08B 21/18 | (2006.01) |
|---|---|
| G08B 17/10 | (2006.01) |
| H02M 1/00 | (2006.01) |
| G01N 33/00 | (2006.01) |
| G01N 27/62 | (2021.01) |
| G01N 21/17 | (2006.01) |

(52) U.S. Cl.
CPC .............. *G08B 17/10* (2013.01); *G01N 21/17* (2013.01); *G01N 27/62* (2013.01); *G01N 33/004* (2013.01); *H02M 1/00* (2013.01); *G01N 2201/062* (2013.01); *H02M 1/0032* (2021.05); *H02M 1/0045* (2021.05)

(58) Field of Classification Search
CPC ........ G08B 17/10; G01N 21/17; G01N 27/62; G01N 33/004; G01N 2201/062; H02M 1/00; H02M 2001/0032; H02M 2001/0045
See application file for complete search history.

(56) References Cited

U.S. PATENT DOCUMENTS

2006/0184847 A1* 8/2006 Song .................. G01R 31/3172
                                                               714/724
2011/0283141 A1* 11/2011 Lee .......................... G06F 1/32
                                                               714/30
(Continued)

FOREIGN PATENT DOCUMENTS

| RU | 113392 U1 | 10/2012 |
|---|---|---|
| WO | 2013045446 A1 | 4/2013 |

OTHER PUBLICATIONS

PCT International Search Report No. PCT/US 2021/026797, dated Jul. 15, 2021, 3 pages.

*Primary Examiner* — Munear T Akki
(74) *Attorney, Agent, or Firm* — Ray A. King; Charles A. Brill; Frank D. Cimino

(57) ABSTRACT

A system on a chip (SoC) for smoke detection includes power regulator circuits coupled to respective pins and analog sensor amplifier circuits that are each coupled to a respective pin of the pins coupled to the power regulator circuits. A first analog sensor amplifier circuit of the analog sensor amplifier circuits has a photoelectric amplifier circuit, a first LED driver and a second LED driver. The SoC also has a digital core that includes a digital logic circuit, register bits, and an MCU communication circuit. The MCU communication circuit is coupled to a data pin, the register bits are coupled to control or modify operation of the power regulator circuits and the analog sensor amplifier circuits, and the register bits are operable to be written to by an MCU.

54 Claims, 14 Drawing Sheets

(56) References Cited

U.S. PATENT DOCUMENTS

2013/0116534 A1\* 5/2013 Woo ..................... A61B 5/0245
                                                        600/391
2014/0327630 A1   11/2014 Burr et al.
2017/0287309 A1\* 10/2017 Gerbus ................ G08B 21/182

\* cited by examiner

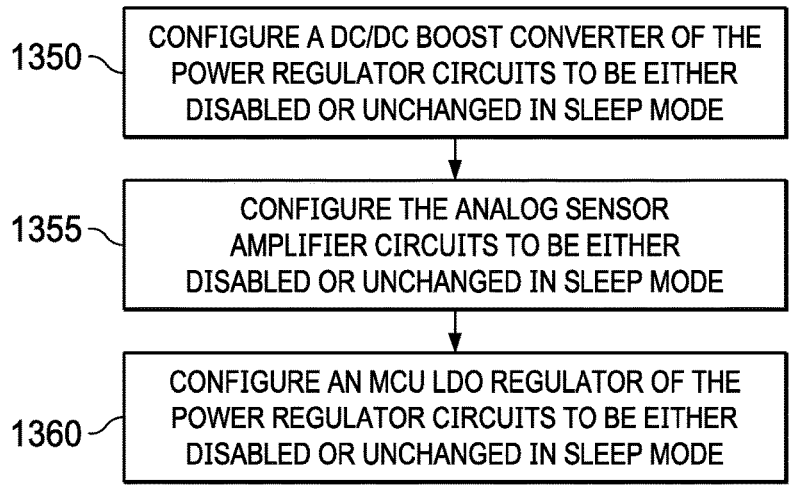
FIG. 13C
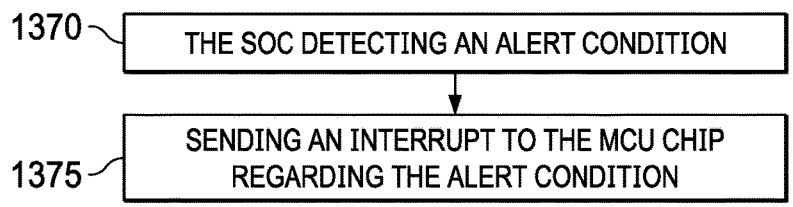
FIG. 13D
FIG. 13E

SYSTEM-ON-CHIP FOR SMOKE ALARM

BACKGROUND

Smoke alarms, also referred to as smoke detectors or smoke detection devices, require a variety of interconnected circuit blocks for standard operation. Depending on the target market, which can be either commercial or residential, these circuit blocks may include amplifier circuits for sensors, communication circuits with a microcontroller unit (MCU), a horn driver circuit, an interconnect circuit for communications with other smoke detection devices in the home, a signaling line circuit (SLC) for communications with a commercial fire alarm system, and power regulator circuits to provide multiple voltages from either a wired direct current (DC) source or from a battery that may have one of a variety of voltages. These circuit blocks must be implemented in a size, power, and cost constrained system that, in some cases, must have a 10-year sealed battery life. New implementations are needed for cost-effective solutions meeting the latest smoke detection standards.

SUMMARY

Disclosed embodiments provide a highly integrated system on a chip (SoC) that replaces multiple ICs and discrete components in a smoke detection device. The SoC is combined with a power source, desired sensors, desired communication connections, and an MCU integrated circuit (IC)—which is a separate IC to offer greater flexibility—to provide a smoke detection device. A digital core on the SoC allows the external microcontroller to control each of the integrated blocks on the SoC. For example, sensor amplifiers may have adjustable gain, power regulators may have adjustable voltages, and drivers may have adjustable current. The control provided thereby improves system efficiency and amplifier performance. Additionally, the digital core implements power-saving through a sleep mode, as well as fault-monitoring, such as under-voltage and over-temperature fault detection.

The SoC is designed to be utilized in multiple different configurations. The power regulator circuits, which include a number of low dropout (LDO) regulators, are coupled in a manner that allows the single SoC to be combined with multiple different power supplies, such as a battery having a voltage that is between 3 V and 12 V, an AC/DC power converter, or an SLC. The SoC includes multiple analog sensor amplifier circuits, e.g., a photoelectric amplifier circuit, a carbon monoxide (CO) amplifier circuit, and an ionization amplifier circuit, which can be electronically configured to be active or inactive in a given situation. Two light emitting diode (LED) drivers are provided on the chip, with the capability to use one or both. An interconnect driver/receiver circuit and a piezoelectric horn driver circuit, which are used in residential smoke detectors, share pins on the SoC with an SLC transmit circuit and SLC receive circuit, which is used in commercial smoke detectors, with either the interconnect driver/receiver circuit or the SLC transmit circuit and SLC receive circuit being active in a given smoke detector.

In one aspect, an embodiment of an SoC for smoke detection is disclosed. The SoC includes power regulator circuits; analog sensor amplifier circuits, each coupled to receive a respective upper power supply from the power regulator circuits, a first analog sensor amplifier circuit of the analog sensor amplifier circuits having a photoelectric amplifier circuit, a first LED driver and a second LED driver; an MCU communication circuit; and an external communication circuit.

In another aspect, an embodiment of a smoke detection device is disclosed. The smoke detection device includes a system on a chip (SoC) that includes power regulator circuits, analog sensor amplifier circuits, each coupled to receive a respective upper power supply from the power regulator circuits, a first analog sensor amplifier circuit of the analog sensor amplifier circuits having a photoelectric amplifier circuit, a first LED driver and a second LED driver, an MCU communication circuit, and an external communication circuit; sensors, each sensor of the sensors coupled to a respective one of the analog sensor amplifier circuits; a DC power supply coupled to the power regulator circuits; and a microcontroller unit (MCU) chip that includes an upper power supply input, a digital processor, an analog to digital converter (ADC), an SoC communication circuit, and a general purpose I/O circuit, the upper power supply input on the MCU chip being coupled to receive power from the power regulator circuits.

In yet another aspect, an embodiment of a process of operating a smoke detector is disclosed. The process includes, at startup, providing power to a system on a chip (SoC) that includes communication circuits, analog sensor amplifier circuits, and power regulator circuits; determining a first voltage for a microcontroller unit (MCU) chip attached to the SoC; and the SoC providing power to the MCU chip at the first voltage.

BRIEF DESCRIPTION OF THE DRAWINGS

Embodiments of the present disclosure are illustrated by way of example, and not by way of limitation, in the figures of the accompanying drawings in which like references indicate similar elements. It should be noted that different references to "an" or "one" embodiment in this disclosure are not necessarily to the same embodiment, and such references may mean at least one. Further, when a particular feature, structure, or characteristic is described in connection with an embodiment, it is submitted that it is within the knowledge of one skilled in the art to effect such feature, structure, or characteristic in connection with other embodiments whether or not explicitly described. As used herein, the term "couple" or "couples" is intended to mean either an indirect or direct electrical connection unless qualified as in "communicably coupled" which may include wireless connections. Thus, if a first device couples to a second device, that connection may be through a direct electrical connection, or through an indirect electrical connection via other devices and connections.

The accompanying drawings are incorporated into and form a part of the specification to illustrate one or more exemplary embodiments of the present disclosure. Various advantages and features of the disclosure will be understood from the following Detailed Description taken in connection with the appended claims and with reference to the attached drawing figures in which:

FIGS. 13A-13E depict additional elements that may be part of the process of FIG. 13.

DETAILED DESCRIPTION OF THE DRAWINGS

Specific embodiments of the invention will now be described in detail with reference to the accompanying figures. In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

Figure 1:
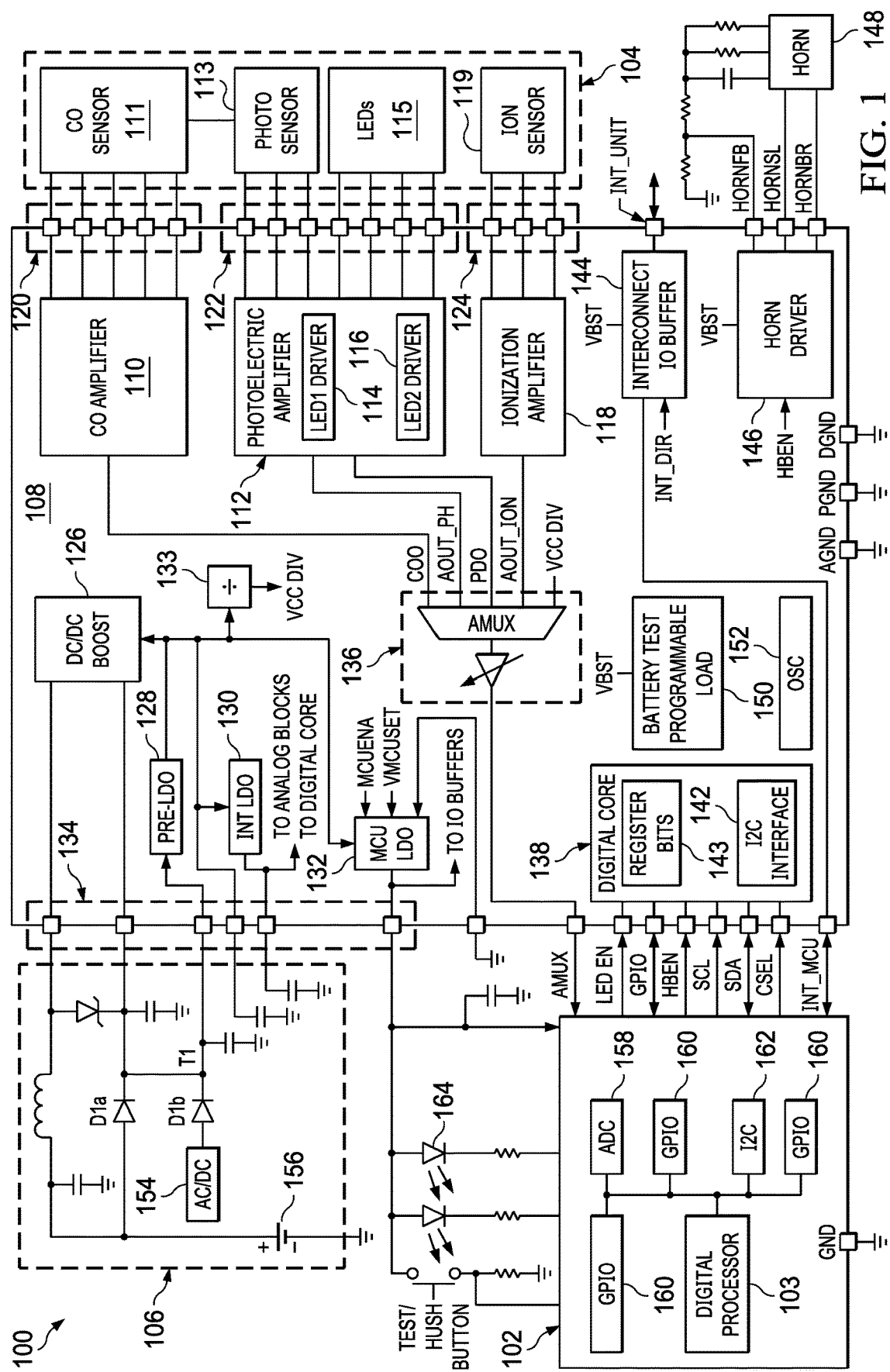
FIG. 1 depicts an example of a smoke detection device according to an embodiment of the disclosure.

FIG. 1 depicts a smoke detection device 100 according to an embodiment of the disclosure. Smoke detection device 100 broadly includes the following elements:

An MCU chip 102 to provide overall control of the smoke detection device 100;

Sensors 104, which can include but are not limited to, an ionization sensor, a photoelectric sensor, one or more LEDs, and a CO sensor;

A DC power supply 106; and

An SoC 108 that includes analog sensor amplifier circuits for the sensors, power regulator circuits to provide appropriate voltages for the needs of the smoke detection device 100, and communication circuits for communications between the SoC 108 and the MCU chip 102 and with external circuitry or people.

Within SoC 108, the analog sensor amplifier circuits include a CO amplifier circuit 110, a photoelectric amplifier circuit 112 that includes a first LED driver 114 and a second LED driver 116, and an ionization amplifier circuit 118. The CO amplifier circuit 110 is coupled to a group of CO pins or terminals 120; the photoelectric amplifier circuit 112, including the first LED driver 114 and second LED driver 116, is coupled to a group of photo pins or terminals 122; and the ionization amplifier circuit 118 is coupled to a group of ion pins or terminals 124. Details of the analog sensor amplifier circuits are discussed with regard to FIGS. 2-5.

The power regulator circuits include a DC/DC boost converter 126, a pre-LDO regulator 128, an internal LDO regulator 130, an MCU LDO regulator 132 and a voltage divider 133. The power regulator circuits are coupled to a group of power regulator pins or terminals 134 and are discussed with regard to FIG. 7. The communication circuits include two types of communication: communication with the MCU chip 102 and communication with the external world. Communication between MCU chip 102 and SoC 108 is performed using an analog multiplexor circuit 136 and digital core circuit 138, which includes a serial MCU communication circuit 142 and registers that include register bits 143. In one embodiment, the serial MCU communication circuit 142 is an Inter-Integrated Circuit (I2C) interface that utilizes the I2C communication protocol. Analog multiplexor circuit 136 has a respective input coupled to the output of each of the analog sensor amplifier circuits and an output coupled to analog MUX pin or terminal AMUX and is discussed with regard to FIG. 6. Digital core circuit 138 has a first input coupled to an LED enable pin or terminal LEDEN, a second input coupled to a general purpose input/output (I/O) pin or terminal GPIO, and a third input coupled to a horn block enable pin or terminal HBEN. Serial MCU communication circuit 142 within digital core circuit 138 has a first input coupled to a serial clock pin or terminal SCL, a second input coupled to a serial data pin or terminal SDA, and a third input coupled to a device address select pin or terminal CSEL. Digital core circuit 138 and serial MCU communication circuit 142 are coupled to each other, allowing MCU chip 102 to write to registers in the digital core circuit 138 using the serial MCU communication circuit 142.

External communications are needed in order to signal alarms to persons in an area where smoke is detected, communicate with other smoke detection devices in a residence, or to a fire alarm control panel (FACP) in a commercial site. External communication circuits can include interconnect I/O buffer 144, horn driver circuit 146, which controls piezoelectric horn 148, and a signaling line circuit (SLC), which is not specifically shown in FIG. 1. Interconnect I/O buffer 144 and horn driver circuit 146 are used in residential smoke detection devices, while an SLC is used in commercial smoke detection devices. Interconnect I/O buffer 144 is discussed with regard to FIG. 8; a horn driver circuit 146 for a three-terminal piezoelectric horn and a horn driver circuit 146 for a two-terminal piezoelectric horn are discussed with regard to FIG. 9A and FIG. 9B respectively; and an SLC is discussed with regard to FIG. 10. Three ground pins are shown on SoC 108: an analog ground pin AGND, a digital ground pin DGND, and a power ground pin PGND.

SoC 108 also includes a battery test circuit 150 with programmable load and an oscillator 152. The battery test circuit 150 is used to check the integrity of a battery that is connected to the SoC 108. When battery test circuit 150 is enabled, a load that in one embodiment is programmable from 10 mA to 20 mA is connected to an output voltage from the DC/DC boost converter 126. This load emulates the horn driver current draw during an alarm condition. Oscillator 152 is internal and is enabled when either the DC/DC boost converter 126 or the photoelectric amplifier circuit 112 is enabled.

Both advantages and inherent difficulties are attendant on the high level of integration shown in SoC 108. Smoke alarms often require many different analog blocks, e.g., drivers and amplifiers. Different models of a smoke alarm may require many of the same blocks, which can also be provided as multiple discrete IC chips, but the different models may differ in the sensors, the power supply, and the channels for communication with external circuitry or people. The disclosed SoC 108 integrates all of the common blocks into a single chip, but does so in a manner that allows different models of smoke detection devices to be produced with a variety of attached sensors, different power supplies, different MCUs, and different communication channels, all using the same SoC 108 to provide the circuitry to tie the remaining elements together.

Of course the high level of integration provides a new set of problems to be solved. For example, sensor signals, which may provide only nano-amperes of current, can be very sensitive to the presence of electronic noise. When sensor amplifiers are combined with noisy elements like the DC/DC boost converter 126, the layout must be carefully performed to provide isolation of noisy circuits from the sensitive circuits, e.g., the ionization amplifier circuit 118 and in some cases, the photoelectric amplifier circuit 112.

At the same time, new regulations from Underwriters Laboratories (UL) require new elements, such as the ability to distinguish smoke from different types of fires and limiting false alarms by incorporating newer sensor technologies, all of which must be performed while providing a very low power device that can run for ten years on a 3.6 V lithium battery. This means that the biasing circuits are used with very low currents, which are very sensitive to clock signals, noise, etc. A great deal of attention is necessary to get the desired performance. Providing low power usage meant slowing the clock down and keeping the number of gates to a minimum in order to keep the power requirements of the SoC 108 as low as possible.

Because a single SoC 108 can be used with different sensors and different power supplies, many of the analog sensor amplifier circuits and the DC/DC boost converter 126 are electronically configurable, e.g., when a given smoke detection device 100 does not include an ionization sensor, the ionization amplifier circuit 118 can be electronically disabled. Similarly, SoC 108 can be utilized with an interconnect I/O buffer 144 and horn driver circuit 146 or else utilized with a signaling line circuit (not specifically shown in this figure). As is explained in greater detail below, these circuits can share pins, because an interconnect buffer and an SLC are never used at the same time.

Continuing to look at smoke detection device 100, the DC power supply 106 is depicted using an AC/DC converter 154 with a low-voltage battery 156 for use when the mains power fails. Other configurations that can be utilized are discussed with regard to FIG. 7. As shown in smoke detection device 100, sensors 104 include an ionization sensor 119, a photoelectric sensor 113, one or more LEDs 115, and a CO sensor 111. These sensors are discussed in conjunction with their corresponding amplifier circuits in FIGS. 2-5.

MCU chip 102 is used to control the operation of each block in SoC 108 and has been provided in smoke detection device 100 as a separate IC from SoC 108 in order to provide greater flexibility in the smoke detection device 100. MCU chip 102 has an MCU upper power supply input, a digital processor 103, an ADC 158, one or more general purpose input/output (I/O) circuits 160, and a serial SoC communication circuit 162, which in the embodiment shown uses the I2C communication protocol. The MCU upper power supply input is coupled to the output of MCU LDO regulator 132 and receives all necessary power from SoC 108. Digital processor 103 receives programming inputs from a user and data collected by SoC 108 and makes decisions as to actions needed. ADC 158 has an input that is coupled to the analog multiplexor output pin AMUX. The serial MCU communication circuit 142 in SoC 108 is coupled to the serial SoC communication circuit 162 in MCU chip 102 through three pins: serial clock pin SCL, serial data pin SDA, and device address select pin CSEL. As will be discussed throughout the present application, the power regulator circuits and the analog sensor amplifier circuits can receive control bits or bit flags that control or modify the operation of the respective circuits. These control bits or bit flags can be stored in the register bits or bit flags 143 in digital core circuit 138. The serial MCU communication circuit 142 and serial SoC communication circuit 162 provides a means for MCU chip 102 to write to the register bits or bit flags 143 in digital core circuit 138 and provide control of SoC 108 thereby. General purpose I/O circuit 160 has a first output that can be coupled to control LED indicators 164, a second output coupled to LED enable pin LEDEN, and a third output coupled to horn enable terminal HBEN. A first two-way communication line is coupled to digital core circuit 138 on SoC 108 through general purpose I/O terminal GPIO and a second two-way communication line is coupled to interconnect-to-MCU terminal INT_MCU for communication with the external circuitry.

Figure 2:
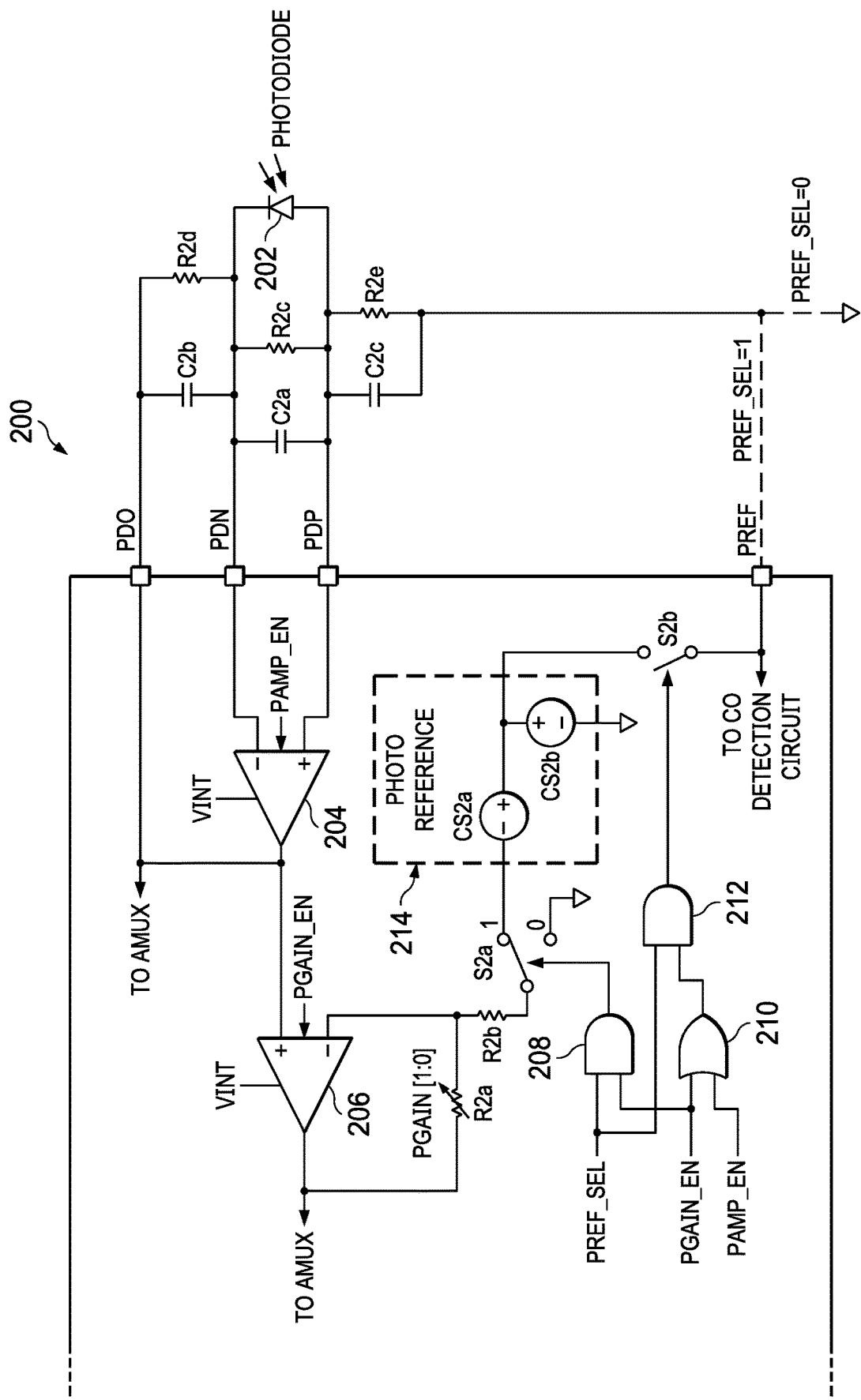
FIG. 2 depicts a photoelectric amplifier circuit that can be used in the smoke detection device of FIG. 1 according to an embodiment of the disclosure.

FIG. 2 depicts a photoelectric amplifier circuit 200 that may be part of photoelectric amplifier circuit 112 in the SoC 108. Photoelectric amplifier circuit 200 connects to a photodiode 202 and has two stages—a photo input amplifier 204 and a photo gain amplifier 206. The output of photo input amplifier 204 and the output of photo gain amplifier 206 are connected to the analog multiplexor circuit 136, which passes the values to the ADC 158 and thence to MCU chip 102. The disclosed configuration provides a high dynamic range for the photodiode signal chain, because the photo gain amplifier 206 is adjustable on-the-fly.

Photo input amplifier 204 has an upper power supply input coupled to the internal LDO regulator 130, a photo-in inverting input, a photo-in non-inverting input, an photo-in output, and a photo-in enable input, the photo-in inverting input coupled to a photodiode negative pin PDN, the photo-in non-inverting input coupled to a photodiode positive pin PDP, the photo-in output coupled to a first input of the analog multiplexor circuit 136 and to photodiode output pin PDO, and the photo-in enable input coupled to receive a photo input amplifier control bit PAMP_EN. Photo gain amplifier 206 has an upper power supply input coupled to internal LDO regulator 130, a photo-gain non-inverting input, a photo-gain inverting input, a photo-gain enable input, and a photo-gain output, the photo-gain non-inverting input coupled to the output of photo input amplifier 204, the photo-gain enable input coupled to receive a photo gain amplifier control bit PGAIN_EN, and the photo-gain output coupled to a second input of the analog multiplexor circuit 136 and to the photo-gain inverting input through a first photo resistor R2$a$, which is an adjustable resistor.

A first photo AND gate 208 has a first input coupled to receive a photo reference select bit PREF_SEL, a second input coupled to receive the photo gain amplifier control bit PGAIN_EN, and an output. A first photo OR gate 210 has a first input coupled to receive the photo gain amplifier control bit PGAIN_EN, a second input coupled to receive the photo input amplifier control bit PAMP_EN and an output. A second photo AND gate 212 has a first input coupled to receive the photo reference select bit PREF_SEL, a second input coupled to receive the output of the first photo OR gate 210 and an output.

A photo reference circuit 214 has a photo-ref input and a photo-ref output. A first photo voltage source CS2*a* is coupled between the photo-ref input and the photo-ref output and a second photo voltage source CS2*b* is coupled between the photo-ref input and the ground plane. A first photo switch S2*a* is coupled to the photo-gain inverting input through a second photo resistor R2*b*. First photo switch S2*a* selectively couples the photo-gain inverting input to either photo reference circuit 214 or to the ground plane; the output of the first photo AND gate 208 is coupled to control the first photo switch S2*a*. A second photo switch S2*b* has first terminal that is coupled to the photo-ref input and a second terminal that is coupled to the photo reference pin or terminal PREF and to CO amplifier circuit 400, seen in FIG. 4. Second photo switch S2*b* is controlled by the output of second photo AND gate 212. In one embodiment, first photo voltage source CS2*a* passes a voltage of about 5 mV and second photo voltage source CS2*b* passes a voltage of about 50 mV.

During operation of photoelectric amplifier circuit 200, the photodiode 202 has an anode coupled to the photodiode positive pin PDP and a cathode coupled to the photodiode negative pin PDN. A first photo capacitor C2*a* and a third photo resistor R2*c* are coupled in parallel between the photodiode positive pin PDP and the photodiode negative pin PDN. A second photo capacitor C2*b* and a fourth photo resistor R2*d* are coupled in parallel between the photodiode output pin PDO and the photodiode negative pin PDN. A third photo capacitor C2*c* and a fifth photo resistor R2*e* are coupled in parallel between the photodiode positive pin PDP and a ground plane. In one embodiment, the third photo capacitor C2*c* and the fifth photo resistor R2*e* are coupled in parallel between the photodiode positive pin PDP and the photo reference pin PREF. In one embodiment, first photo capacitor C2*a* has a capacitance of 7 pF, second capacitor C2*b* has a capacitance of 10 pF, third capacitor C2*c* has a capacitance of 10 pF, third photo resistor R2*c* has a resistance of 470 kω, fourth photo resistor R2*d* has a resistance of 1.5 Mω, and fifth photo resistor R2*e* has a resistance of 1.5 Mω.

The photo input amplifier 204 is a wide-bandwidth, low-offset operational-amplifier designed for amplifying photodiode currents. Negative feedback causes the photodiode to conduct with zero voltage bias. The input stage has the option of being referenced to the ground plane GND or to photo reference pin PREF. Photo reference pin PREF is a reference that is normally pulled to the voltage on an internal LDO output pin VINT and that can be configured by the MCU to 50 mV. The 50-mV reference keeps the input amplifier in a linear operating region when no signal is applied, improving the speed and zero-current sensitivity of the amplifier.

The photo-current flows through fifth photo resistor R2*e*, which is coupled between photodiode positive pin PDP and either the ground plane GND or photo reference pin PREF and through fourth photo resistor R2*d*, which is coupled between photodiode negative pin PDN and photodiode output pin PDO. These two resistors, which are matched, determine the gain of the input stage. Second photo capacitor C2*b* and third photo capacitor C2*c* compensate the op-amp feedback loop for optimal response. In one embodiment, second photo capacitor C2*b* and third photo capacitor C2*c* can be 5 pF when the input amplifier is referenced to photo reference pin PREF and can be 10 pF when the input amplifier is referenced to the ground plane GND. The third photo resistor R2*c* and the first photo capacitor C2*a*, which in one embodiment are 470 kΩ and 7 pF respectively, stabilize the feedback loop.

The photo gain amplifier 206 is also high-bandwidth and low noise and further amplifies the photodiode signal. Photo gain amplifier 206 is adjustable on-the-fly using the I2C interface 142. In one embodiment, photo gain amplifier 206 has four settings and can be set to amplify by five times, eleven times, twenty times, or thirty-five times. The photo gain amplifier 206 can be referenced to either the ground plane or photo reference pin PREF using the photo reference select bit PREF_SEL. When the photo reference pin PREF is used, the output of photo gain amplifier 206 is kept above 50 mV. Referencing the photo gain amplifier 206 to photo reference pin PREF causes the 50 mV reference voltage to change depending on the signal level at photodiode output pin PDO. Because the reference is changing with the signal level, the gain is slightly different. The output of photo gain amplifier 206 with zero photo-current varies when the gain setting changes to keep the output above 50 mV.

Figure 3:
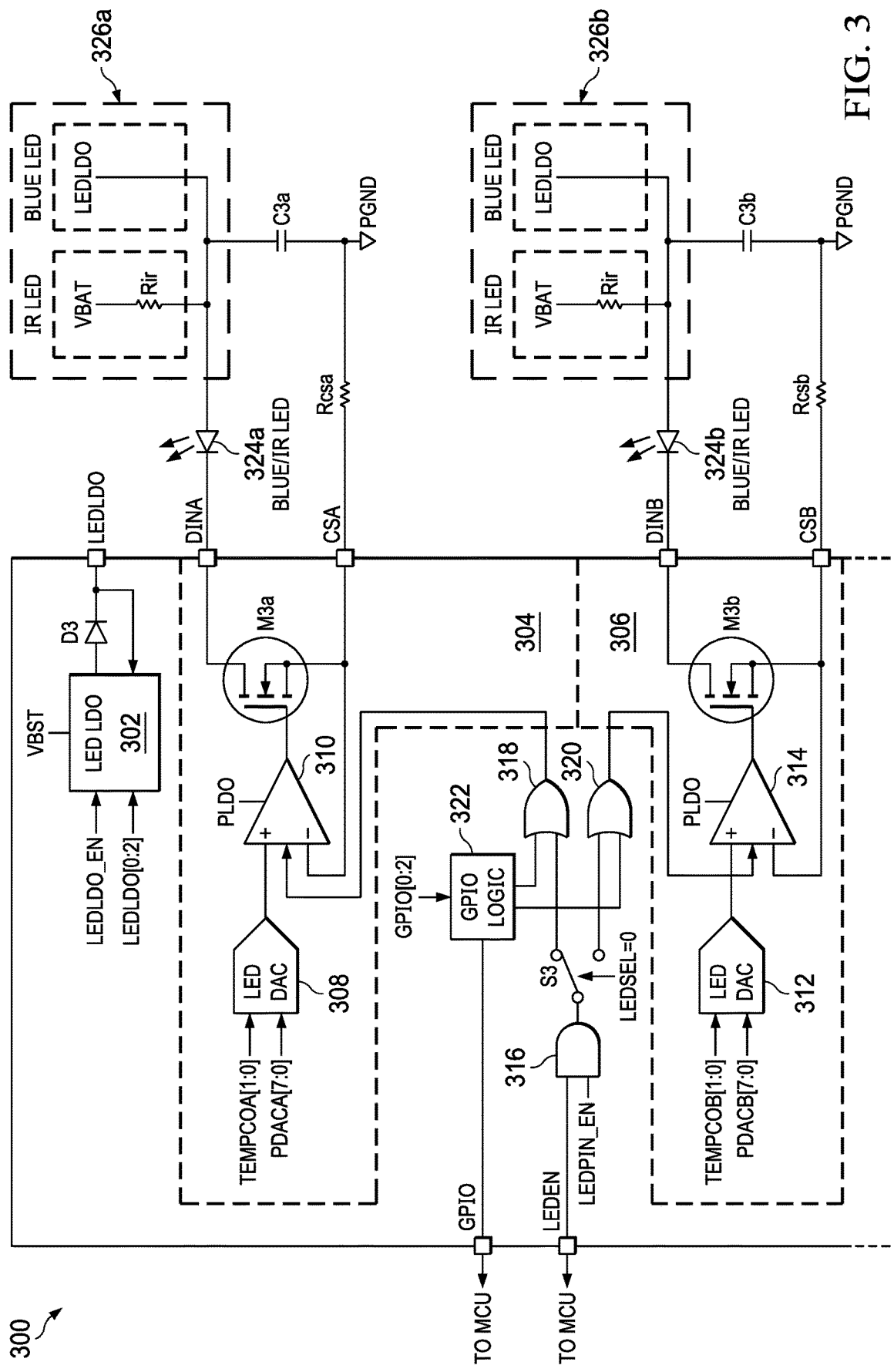
FIG. 3 depicts an LED driver circuit that can be used in the smoke detection device of FIG. 1 according to an embodiment of the disclosure.

FIG. 3 depicts an LED driver circuit 300 that can be used in smoke detection device 100. LED driver circuit 300 includes an LED LDO regulator circuit 302 that has an upper power supply input coupled to boost pin VBST, a first LED input coupled to an LED LDO enable bit LEDLDO_EN, a second LED input coupled to an LED LDO register LEDLDO[0:2], an output coupled to an LED LDO pin LEDLDO through an LED diode D3, and a third input coupled to LED LDO pin LEDLDO. LED Driver circuit 300 also contains a first LED driver 304 and a second LED driver 306.

First LED driver 304 includes a first LED DAC 308, a first LED amplifier 310 and a first LED NFET M3*a*. First LED DAC 308 has a first input coupled to first temperature coefficient bits TEMPCOA[1:0], a second input coupled to a first current setting register PDACA[7:0], and an output. In one embodiment, first temperature coefficient bits TEMPCOA[1:0] offers a choice of four different temperature coefficients that can be selected and first current setting register PDACA[7:0], which contributes to the value of current on the first LED. First LED amplifier 310 has an upper supply voltage input coupled to the pre-LDO output pin PLDO, a non-inverting input coupled to the output of first LED DAC 308, an inverting input coupled to first LED current sense pin CSA, an enable input, and an output. First LED NFET M3*a* has a drain coupled to first LED current sink pin DINA, a source coupled to first LED current sense pin CSA, and a gate coupled to the output of first LED amplifier 310.

Second LED driver 306 includes a second LED DAC 312, a second LED amplifier 314 and a second LED NFET M3*b*. Second LED DAC 312 has a first input coupled to second temperature coefficient bits TEMPCOB[1:0], a second input coupled to a second current setting register PDACB[7:0], which again contributes to the value of the current on the second LED, and an output. Second LED amplifier 314 has an upper supply voltage input coupled to the pre-LDO output pin PLDO, a non-inverting input coupled to the output of second LED DAC 312, an inverting input coupled to second LED current sense pin CSB, an enable input, and an output. Second LED NFET M3*b* has a drain coupled to second LED current sink pin DINB, a source coupled to second LED current sense pin CSB, and a gate coupled to the output of second LED amplifier 314.

The operation of first LED driver 304 and second LED driver 306 is controlled through the action of an LED AND gate 316, a first LED OR gate 318, a second LED OR gate 320, and general purpose I/O logic 322. General purpose I/O logic 322 has a first input coupled to general purpose I/O pin GPIO, a second input coupled to general purpose I/O register GPIO[0:2], a first output and a second output. LED AND gate 316 has a first input coupled to LED enable pin LEDEN, a second input coupled to LED pin enable bit LEDPIN_EN and an output coupled to an LED switch S3. First LED OR gate 318 has a first input that is coupled to the first output of general purpose I/O logic 322, a second input, and an output coupled to the enable input of first LED amplifier 310. Second LED OR gate 320 has a first input, a second input that is coupled to the second output of general purpose I/O logic 322, and an output coupled to the enable input of second LED amplifier 314. The output of LED AND gate 316 can be selectively coupled either to the second input of first LED OR gate 318 or to the first input of second LED OR gate 320 depending on the value of an LED selection bit LEDSEL.

When both the first LED driver 304 and the second LED driver 306 are utilized in a specific application, one attached LED is generally a blue LED and the other is generally an infrared LED. A first LED 324a has a cathode coupled to first LED current sink pin DINA and an anode coupled to a first LED voltage source 326a and to a first terminal of a first LED capacitor C3a. A second terminal of first LED capacitor C3a is coupled to the power ground pin PGND. A first LED current sense resistor Rcsa is coupled between the first LED current sense pin CSA and the power ground pin PGND. A second LED 324b has a cathode coupled to second LED current sink pin DINB and an anode coupled to a second LED voltage source 326b and to a first terminal of a second LED capacitor C3b. A second terminal of second LED capacitor C3b is coupled to the power ground pin PGND. A second LED resistor Rcsb is coupled between the second LED current sense pin CSB and the power ground pin PGND. The power used to provide the first LED voltage source 326a and the second LED voltage source 326b depends on the type of LED used. For an infrared LED, the LED voltage source 326x is coupled to the battery through a third LED resistor Rir, and for a blue LED, the LED voltage source 326x is coupled to the LED LDO pin LEDLDO. In one embodiment, third LED resistor Rir has a resistance of 1 kΩ and each of first LED capacitor C3a and second LED capacitor C3b has a capacitance of 100 µF.

The first LED driver 304 and the second LED driver 306 are current regulated, temperature compensated, and adjustable with an 8-bit DAC. When an LED driver is enabled, the voltage on the respective current sense pin CSx is regulated using the values provided to a respective LED DAC 308, 312 and the resistance on the respective current sense resistor Rcsx. The first LED driver 304 and the second LED driver 306 are separately enabled using the LED enable pin LEDEN and the LED enable bit LEDPIN_EN. Both the pin and bit must be high for the selected LED driver to operate. The LED select bits LEDSEL can be used to determine the driver to which the signal on LED enable pin LEDEN is connected. The general purpose I/O pin GPIO can be used to enable either LED driver.

The LED driver is also temperature compensated to account for reduced LED intensity with increasing temperature. Four temperature compensation settings are available to support a variety of IR and blue LEDs. Temperature compensation is implemented by varying the voltage on the LED current sense pin CSA with temperature, thus the temperature compensation also depends on the respective LED resistor Rcsx. The LED LDO regulator circuit 302 clamps the voltage from the boost pin VBST, blocks reverse current with the integrated LED diode D3, and is current limited to prevent inrush current caused by charging the LED capacitor C3x, which in one embodiment is 100 µF.

Figure 4:
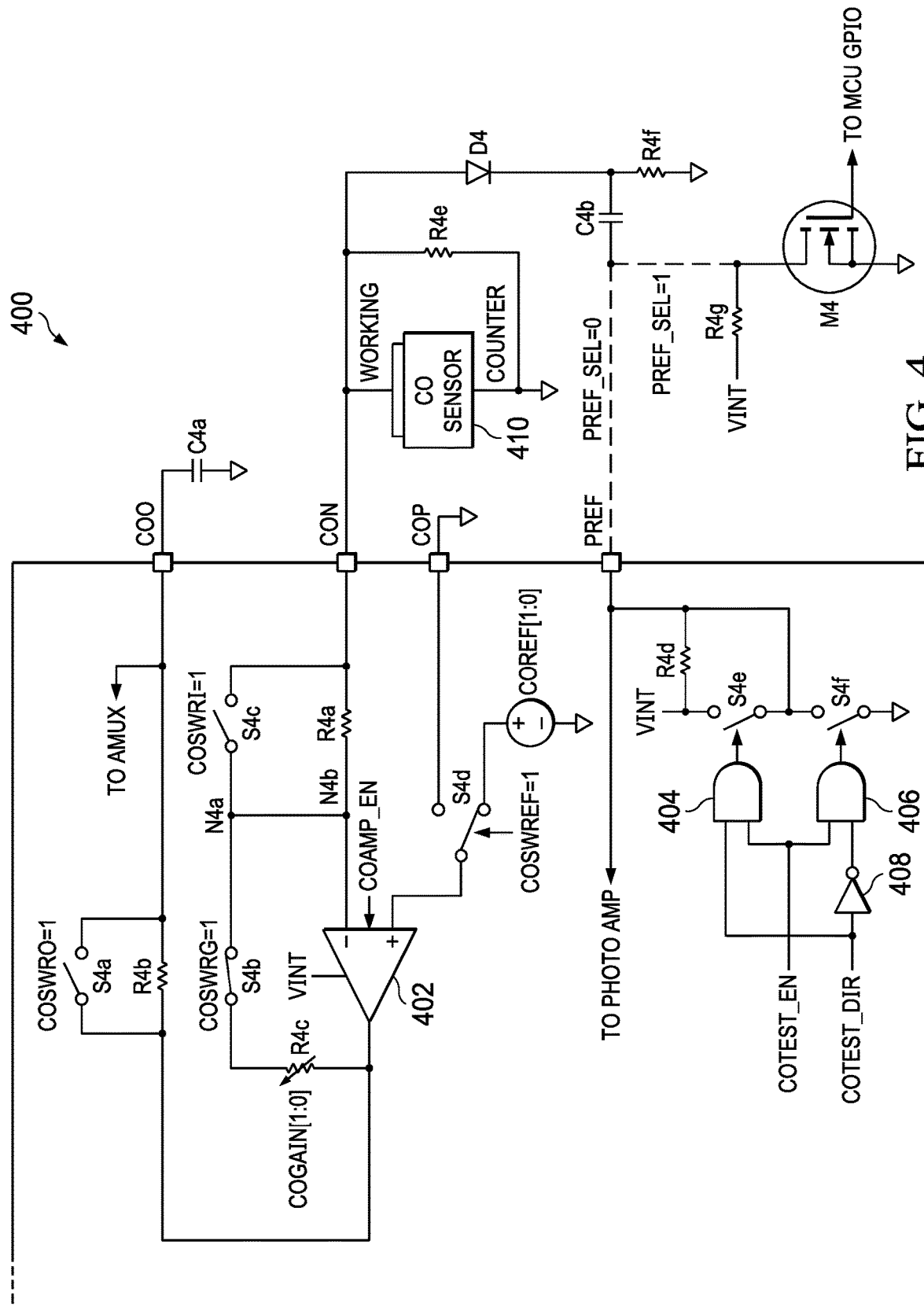
FIG. 4 depicts a CO amplifier circuit that can be used in the smoke detection device of FIG. 1 according to an embodiment of the disclosure.

FIG. 4 depicts a CO amplifier circuit 400 that can be used as the CO amplifier circuit 110. A CO transimpedance amplifier 402 has an upper supply voltage input coupled to the output of the internal LDO regulator 130, a CO amplifier enable input coupled to a CO amplifier enable bit COAMP_EN, a CO inverting input coupled to the CO negative terminal pin CON through a CO input resistor R4a, a CO non-inverting input, and a CO output that is coupled to the CO output pin COO through a CO output resistor R4b. The CO output pin COO is coupled to a third input of the analog multiplexor circuit 136. CO output resistor R4b is coupled in parallel with a CO output switch S4a to allow CO output resistor R4b to be bypassed. A CO gain resistor R4c, which is a variable resistor, a CO feedback switch S4b, and a first CO input switch S4c are also coupled in series between the CO output and the CO negative terminal pin CON, with a first CO node N4a between CO feedback switch S4b and the first CO input switch S4c being coupled to a second CO node N4b between the CO inverting input and the CO input resistor R4a. The CO non-inverting input is coupled to a first terminal of a second CO input switch S4d. The second terminal of the second CO input switch S4d can be selectively coupled to either the CO positive terminal pin COP or to a first terminal of a CO voltage source VS4, where the second terminal of the CO voltage source VS4 is coupled to the ground plane.

In one embodiment, the CO positive terminal pin COP is coupled to a reference voltage of 300 mV (not specifically shown). In one embodiment, CO amplifier circuit 400 also includes a CO connectivity test circuit that includes a first CO AND gate 404 and a second CO AND gate 406. First CO AND gate 404 has a first input that is coupled to receive a CO test output direction bit COTEST_DIR, a second input that is coupled to receive a CO test enable bit COTEST_EN, and an output that is coupled to control a first CO test switch S4e. Second CO AND gate 406 has a first input that is coupled to receive the CO test enable bit COTEST_EN, a second input that is coupled to receive the CO test output direction bit COTEST_DIR through a CO inverter 408, and an output that is coupled to control a second CO test switch S4f. The first CO test switch S4e and the second CO test switch S4f are coupled in series between the internal LDO regulator 130 and the ground plane. A node between first CO test switch S4e and second CO test switch S4f is coupled to the photo reference pin PREF, to the photoelectric amplifier circuit 200, and to the internal LDO regulator 130 through an internal CO resistor R4d, which in one embodiment has a resistance of 200 kΩ.

As shown in FIG. 4, an electrochemical CO sensor 410 is coupled between the CO negative terminal pin CON and the ground plane. A first external CO resistor R4e is coupled in parallel with the electrochemical CO sensor 410 to prevent a charge from accumulating between the terminals of the sensor. CO negative terminal pin CON is also coupled to the ground plane through a CO diode D4 and a second external CO resistor R4f. A first CO capacitor C4a is coupled between the CO output pin COO and the ground plane and in one embodiment, the CO positive terminal pin COP is coupled to the ground plane. The photo reference pin PREF can be coupled in at least two different configurations. In one embodiment, photo reference pin PREF is coupled to a first terminal of a second CO capacitor C4b and a second terminal of the second CO capacitor C4b is coupled to a node between CO diode D4 and second external CO resistor R4f. In one embodiment, photo reference pin PREF is coupled to a drain of a CO NFET M4 and the source of the CO NFET M4 is coupled to the ground plane. A gate of the CO NFET M4 is coupled to be controlled by the MCU chip 102 through a general purpose I/O pin GPIO on the MCU chip. The internal LDO capacitor pin is also coupled to the drain of CO NFET M4 through a third external resistor R4g.

As seen in CO amplifier circuit 400, CO transimpedance amplifier 402 is a low-offset, low-power operational-amplifier with configurable input, gain, and output resistors. Each of the CO input resistor R4a, the CO output resistor R4b, and the CO gain resistor R4c can be bypassed using a respective bit of the COSW register bits if using external resistors is desired. The CO input resistor R4a limits amplifier current during a CO sensor connectivity test. The CO gain resistor R4c amplifies the CO sensor signal. The CO gain resistor R4c can be adjusted by changing the CO gain register bits COGAIN and the CO output resistor R4b can be used to filter the CO amplifier output signal. During operation of the electrochemical CO sensor 410, the CO transimpedance amplifier 402 receives microamps of sensor current from electrochemical CO sensor 410 and the sensor current is converted into a voltage readable by the ADC 158 on the MCU chip 102 through the analog MUX pin AMUX to determine the concentration of CO gas in the air surrounding the sensor.

Figure 5:
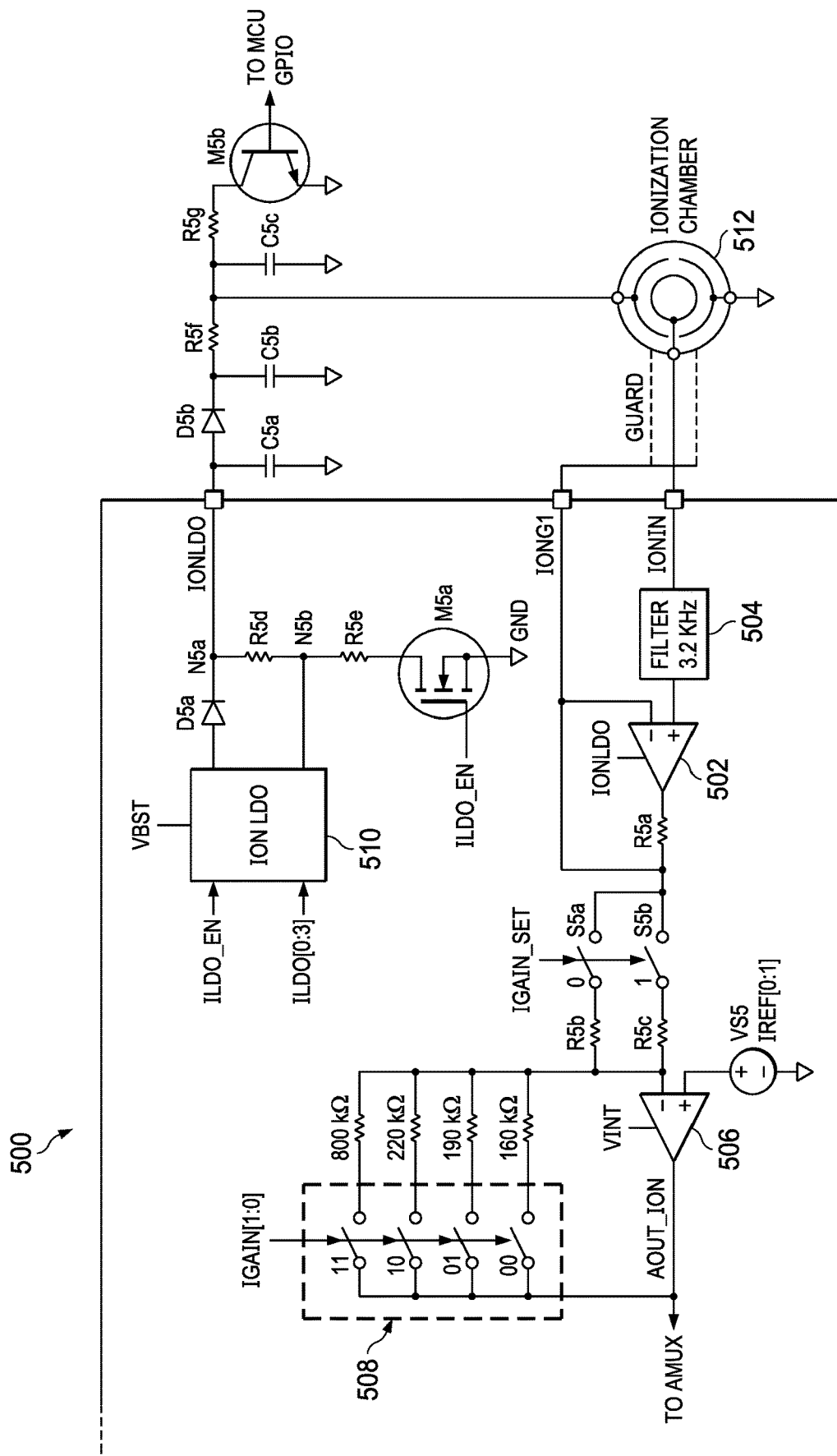
FIG. 5 depicts an ionization amplifier circuit that can be used in the smoke detection device of FIG. 1 according to an embodiment of the disclosure.

FIG. 5 depicts an ionization amplifier circuit 500 that can be used as the ionization amplifier circuit 118 in smoke detection device 100. An ion input amplifier 502 has an ion-in inverting input that is coupled to the ion guard pin IONG1, an ion-in non-inverting input that is coupled to the ion input pin IONIN through a low pass filter 504, which in one embodiment is a 3.2 kHz filter, and an ion-in output that is coupled to a first terminal of a first ion resistor R5a. A second terminal of first ion resistor R5a is coupled to the ion-in inverting input and is further coupled to a first ion switch S5a and a second ion switch S5b; both the first ion switch S5a and the second ion switch S5b are coupled to be controlled by an ion gain setting bit IGAIN_SET. First ion switch S5a couples the ion-in output to an ion-gain inverting input of an ion gain amplifier 506 through a second ion resistor R5b, which in one embodiment has a resistance of 1 MΩ. Second ion switch S5b couples the ion-in output to the ion-gain inverting input through a third ion resistor R5c, which in one embodiment has a resistance of 200 kΩ. An ion-gain non-inverting input of ion gain amplifier 506 is coupled to the ground plane through an ion voltage source VS5 using ion reference voltage settings IREF[0:1] and an ion-gain output of ion gain amplifier 506 is coupled to a fourth input of the analog multiplexor circuit 136 to provide an ion output signal AOUT_ION. The ion-gain output is also coupled to each of a series of ion feedback switches 508 that allow the feedback resistance to be selected using an ion gain setting register IGAIN[1:0]. In one embodiment, a first ion feedback switch is coupled to a first ion feedback resistor having a resistance of 160 kΩ, a second ion feedback switch is coupled to a second ion feedback resistor having a resistance of 190 kΩ, a third ion feedback switch is coupled to a third ion feedback resistor having a resistance of 220 kΩ, and a fourth ion feedback switch is coupled to a fourth ion feedback resistor having a resistance of 800 kΩ. The ion gain amplifier 506 has an upper power supply input coupled to the internal LDO regulator 130.

An ion LDO regulator circuit 510 has an upper supply voltage that is coupled to the boost pin VBST, and ion LDO regulator circuit 510 is further coupled to receive an ion LDO enable bit ILDO_EN and an ion LDO setting ILDO [0:3]. In one embodiment, the ion LDO regulator circuit 510 and LED LDO regulator circuit 302 are the same circuit. The ion LDO regulator circuit 510 is coupled to the ion LDO output pin IONLDO through a first ion diode D5a, with a first ion node N5a being located between the first ion diode D5a and the ion LDO output pin IONLDO. A first ion LDO resistor R5d and a second ion LDO resistor R5e are coupled in series with an ion NFET M5a between the first ion node N5a and the ground plane, with a gate of ion NFET M5a being coupled to receive the ion LDO enable bit ILDO_EN. Ion LDO regulator circuit 510 is also coupled to a second ion node N5b that is between first ion LDO resistor R5d and second ion LDO resistor R5e.

As shown in ionization amplifier circuit 500, an ionization chamber 512 has an upper supply voltage coupled to the ion LDO output pin IONLDO through a second ion diode D5b and a sixth ion resistor R5f and an ion center electrode coupled to the ion input pin IONIN. A guard ring in ionization chamber 512 is coupled to ion guard pin IONG1. A first ion capacitor C5a has a first terminal that is coupled between ion LDO output pin IONLDO and second ion diode D5b and a second ion capacitor C5b has a first terminal that is coupled between second ion diode D5b and sixth ion resistor R5f. The second ion diode D5b and the sixth ion resistor R5f are further coupled in series with seventh ion resistor R5g and NPN transistor M5b between ion LDO output pin IONLDO and the ground plane; a third ion capacitor C5c has a first terminal coupled between sixth ion resistor R5f and seventh ion resistor R5g. Each of first ion capacitor C5a, second ion capacitor C5b, and third ion capacitor C5c have a respective second terminal coupled to the ground plane.

Through the associated pins, ionization amplifier circuit 500 provides ionization chamber 512 with both a bias voltage and the ability to buffer the output signal of ionization chamber 512. In one embodiment, ion LDO regulator circuit 510 has six settings: 7.5 V, 8.0 V, 8.5 V, 9.0 V, 9.5 V, and 10 V. These settings provide the bias voltage for the ionization chamber 512 and power for the ion input amplifier 502. The ion input amplifier 502 connects to the output of ionization chamber 512 to buffer the output voltage and to shield the output from leakage currents. The ion input amplifier 502 is an operational amplifier that is configured for unity gain and optimized for low leakage and low power. The ion input amplifier 502 is not designed to drive any load except the ion gain amplifier 506. Low pass filter 504 is provided to filter electromagnetic interference (EMI).

The ion gain amplifier 506 inverts and shifts the output signal. The ion input amplifier 502 provides an output that is between 1 V and 5 V, which is too high for most microcontrollers. The ion gain amplifier 506 shifts this range of output voltages down to a value between about 0 V and about 2.2 V. Internally, the ion gain amplifier 506 is an operational amplifier that is configured to invert the signal using a programmable reference with a programmable gain. The four reference voltages are 0.71 V, 1.1 V, 2.08 V, and 2.2 V, and the seven gains are 0.16×, 0.19×, 0.22×, 0.8×, 0.95×, 1.1×, and 4×, and are programmable with the ion gain setting bit IGAIN_SET and the ion gain setting register IGAIN[1: 0]. The wide bandwidth of the ion gain amplifier 506 allows this amplifier to be periodically enabled for a short amount of time to capture the ion chamber signal using an external ADC. The ion input amplifier 502 must be powered and enabled for the ion gain amplifier 506 to function properly.

Figure 6:
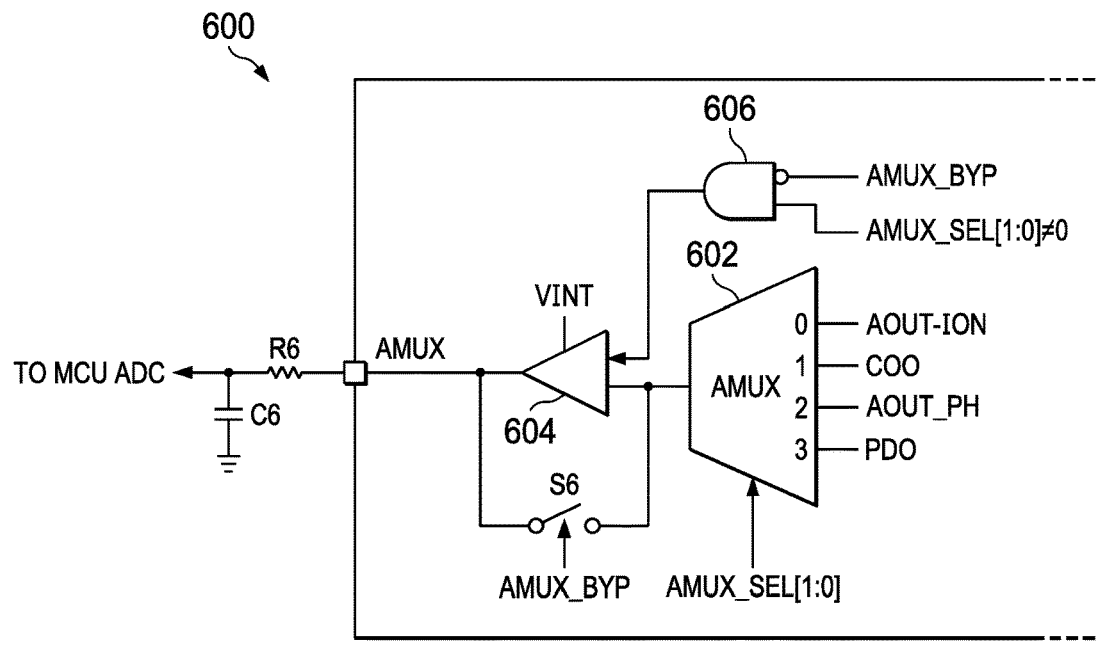
FIG. 6 depicts an analog multiplexor circuit that can be used in the smoke detection device of FIG. 1 according to an embodiment of the disclosure.

FIG. 6 depicts an analog multiplexor circuit 600 that can be used as the analog multiplexor circuit 136. The analog multiplexor circuit 600 includes analog multiplexor (MUX) 602, a MUX amplifier 604, a MUX AND gate 606, and a MUX bypass switch S6. As shown in analog multiplexor circuit 600, analog multiplexor 602 is coupled to receive four signal inputs, although there can be either more or fewer signal inputs. The signal inputs to analog multiplexor 602 are coupled to:

The ion output signal AOUT_ION;
The CO output pin COO;
The photodiode output pin PDO; and
The output AOUT_PH of photo gain amplifier 206.

In addition to the signal inputs, analog multiplexor 602 has an input coupled to receive analog MUX selection bits AMUX_SEL(1:0) and an output. MUX AND gate 606 has a first input coupled to receive an inverse of a MUX bypass bit AMUX_BYP, a second input coupled to receive the MUX selection bits(1:0), and an output. Variable MUX amplifier 604 has a first input coupled to the output of analog multiplexor 602, a second input coupled to the output of MUX AND gate 606, and an output coupled to the analog MUX pin AMUX. A MUX switch S6 is coupled in parallel with variable MUX amplifier 604 between the output of the analog multiplexor 602 and the analog MUX pin AMUX to provide a bypass of the variable MUX amplifier 604. MUX switch S6 is coupled to be controlled by the MUX bypass bit AMUX_BYP. When coupled into a smoke detection device, a MUX capacitor C6 is coupled to the analog MUX pin AMUX and a MUX resistor R6 is coupled between the analog MUX pin AMUX and the ADC 158. In one embodiment, resistor R6 has a resistance of 4.7 kΩ and capacitor C6 has a capacitance of 330 pF.

The analog multiplexor circuit 600 is used to connect the various amplifier outputs to an ADC 158 on MCU chip 102. The MUX amplifier 604 is unity-gain and improves the drive strength and fidelity of the analog signals when connected to an ADC, e.g., ADC 158 and the MUX resistor R6 filters high-frequency noise in the analog signal. The variable MUX amplifier 604 can be bypassed to remove the added offset introduced by the unity-gain amplifier.

Figure 7:
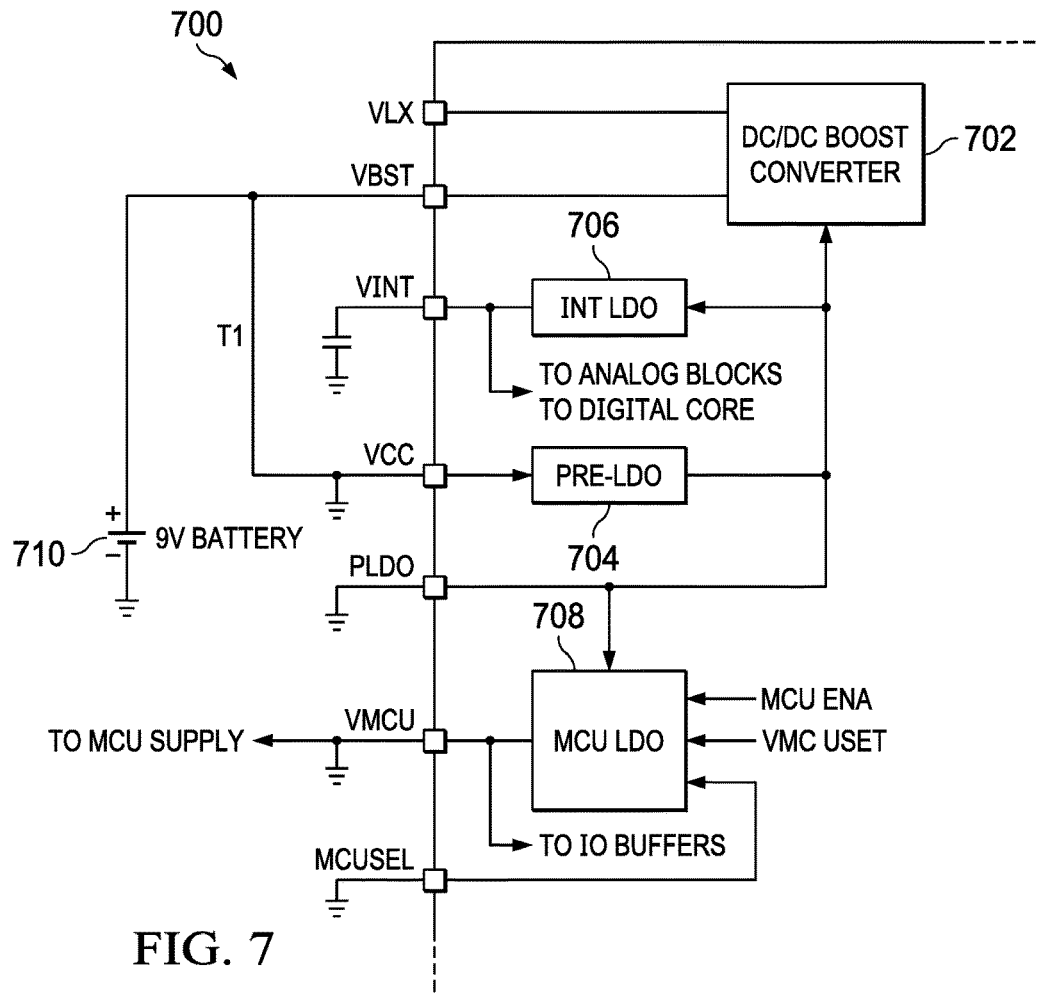
FIG. 7 depicts the power regulator circuits that provide the various voltage levels according to an embodiment of the disclosure.

FIG. 7 depicts the power regulator circuits 700 used to provide each of the voltage levels used by the circuits on the SoC 108, by the attached MCU chip 102, and by the attached external sensors and alarm mechanisms. Power regulator circuits 700 include a DC/DC boost converter 702, a pre-LDO regulator 704, internal LDO regulator 706, and MCU LDO regulator 708. DC/DC boost converter 702 has an upper power supply input, an input coupled to a boost input pin VLX, an output coupled to a boost pin VBST, and can be active when the SoC 108 is operating from a low-voltage battery, e.g. low-voltage battery 156. Pre-LDO regulator 704 has an input that is coupled to a pre-LDO input pin VCC and an output that is coupled to a pre-LDO output pin PLDO and to the upper power supply input of the DC/DC boost converter 702. Internal LDO regulator 706 has an upper power supply input coupled to the output of the pre-LDO regulator 704 and an output coupled to an internal LDO output pin VINT. MCU LDO regulator 708 has an upper power supply input coupled to the output of pre-LDO regulator 704, an output coupled to an MCU LDO output pin VMCU, a first MCU-LDO input coupled to an MCU enable bit MCUENA, a second input coupled to an MCU voltage-setting bit VMCUSET, and a third input coupled to an MCU voltage selection pin MCUSEL.

When coupled in a smoke detection device, a number of different power supply configurations may be used, but they all share a trace T1 in the circuit board (not specifically shown); trace T1 couples the boost pin VBST to the pre-LDO input pin VCC. A first configuration is shown in FIG. 1, in which an AC/DC converter 154 is coupled to trace T1 to provide operating power and a low-voltage battery 156 is coupled to the boost input pin VLX to provide backup power. A first diode D1a prevents a high voltage on boost pin VBST from passing to boost input pin VLX, but when mains power is lost, first diode D1a ensures that power is available to pre-LDO regulator 128, whether or not DC/DC boost converter 126 is active. A second diode D1b is coupled between AC/DC converter 154 and trace T1. In a second configuration, the smoke detection device 100 operates only from the low-voltage battery 156 coupled to the boost input pin VLX, without an AC/DC converter. At startup, diode D1a provides initial power to pre-LDO regulator 128 until DC/DC boost converter 126 becomes active. FIG. 7 depicts a third configuration, in which a high-voltage battery 710, e.g., 8-12 V, is coupled directly to the trace T1 and the boost input pin VLX is left uncoupled. DC/DC boost converter 702 does not become active in this configuration, as it recognizes the high voltage on boost pin VBST. A fourth configuration (not specifically shown) is used in a commercial smoke detection device that utilizes SLC. In this configuration a power line VLINE from an FACP is coupled to trace T1, as well as to communication circuits discussed with regard to FIG. 10.

When the power regulator circuits 700 are operating from a higher voltage coupled to trace T1, such as an AC/DC converter 154 or a high-voltage battery 710, DC/DC boost converter 702 detects that the voltage on boost pin VBST is greater than a programmed output voltage Vpgm and does not attempt to draw power from a backup battery, if one is present. Pre-LDO regulator 704 is designed to receive voltages as high as 15 V, to output a voltage that is regulated to about 4-5 V, and to provide the regulated voltage to the internal LDO regulator 706, DC/DC boost converter 702, and MCU LDO regulator 708. Circuits that require a higher voltage can be coupled to the boost pin VBST, where the higher voltage is available.

When the power regulator circuits 700 are operating from a low-voltage battery, either as a sole power source or when mains power is lost and the backup battery becomes active, DC/DC boost converter 702 receives an input voltage from a low-voltage battery, e.g., 156, which is coupled to boost input pin VLX through inductor L and provides a boosted output voltage on boost pin VBST. DC/DC boost converter 702 monitors the voltage at boost pin VBST and switches only as necessary to maintain a programmed output voltage Vpgm on boost pin VBST. If the programmed output voltage Vpgm is not needed, DC/DC boost converter 702 can be disabled by MCU chip 102 using the serial MCU communication circuit 142 and an appropriate register in digital core circuit 138.

Internal LDO regulator 706 receives power from pre-LDO regulator 704 and further regulates the voltage, which is then provided to various analog circuits and to the digital core. MCU LDO regulator 708 will provide power to an attached MCU, such as MCU chip 102, at a desired voltage level. Initially, the voltage provided to MCU chip 102 is determined by a voltage at the MCU voltage selection pin MCUSEL. In one embodiment, the MCU voltage selection pin MCUSEL can be coupled to any of a) ground, b) left floating, c) internal LDO output pin VINT, and d) ground via a 620 resistor, where each possible connection correlates to an initial voltage provided on MCU LDO output pin VMCU. Once MCU chip 102 is operating, MCU chip 102 can program a different voltage to be provided by MCU LDO regulator 708 using MCU voltage-setting bit VMCUSET.

The output of MCU LDO regulator 708 can also be provided to the interconnect I/O buffers 144.

Because SoC 108 is providing power to MCU chip 102, the two IC chips must coordinate with each other for a low-power or sleep mode. MCU chip 102 can send an instruction to SoC 108 to go to sleep mode, then MCU chip 102 places itself in sleep mode. SoC 108 will leave a timer running while analog circuits and other circuits are placed in low-power mode. After a set period of time, e.g., 2 seconds, MCU enable bit MCUENA is used to instruct MCU LDO regulator 708 to provide power and wake up MCU chip 102. In this manner, smoke detection device 100 can be in sleep mode most of the time, yet wake up every few seconds to run necessary tests, providing ultra-low power use and giving the smoke detection device 100 the ability to run for ten years on a 3.6 V lithium battery.

Figure 8:
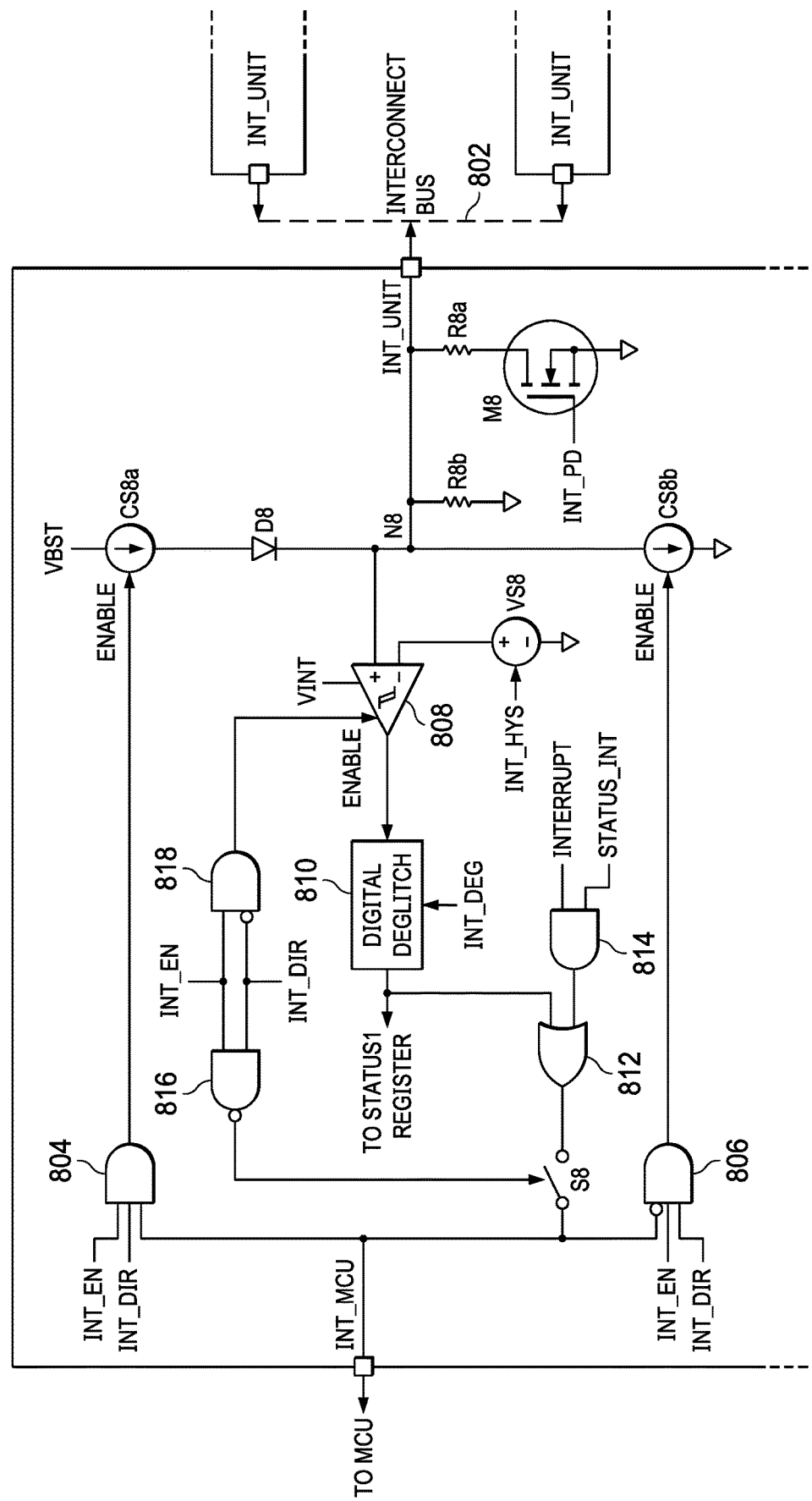
FIG. 8 depicts an interconnect driver/receiver circuit that can be used in the smoke detection device of FIG. 1 according to an embodiment of the disclosure.

FIG. 8 depicts an interconnect driver/receiver circuit 800 that can be used as the interconnect I/O buffer 144. Interconnect driver/receiver circuit 800 has an upper power supply input coupled to the output of DC/DC boost converter 702 and provides two-way serial communication between the MCU chip 102 and a wired interconnect bus 802 through interconnect-to-MCU pin INT_MCU and interconnect-to-bus pin INT_UNIT. A first interconnect AND gate 804 has a first input coupled to an interconnect enable bit INT_EN, a second input coupled to an interconnect direction bit INT_DIR, a third input coupled to the interconnect-to-MCU pin INT_MCU, and an output. A second interconnect AND gate 806 has a first input coupled to an inverse of the value on the interconnect-to-MCU pin INT_MCU, a second input coupled to the interconnect enable bit INT_EN, a third input coupled to the interconnect direction bit INT_DIR, and an output. A first interconnect current source CS8a is coupled in series with an interconnect diode D8 and a second interconnect current source CS8b between the upper power supply input for interconnect driver/receiver circuit 800 and the ground plane. The first interconnect current source CS8a has an input that is coupled to receive an enable signal from the output of first interconnect AND gate 804 and the second interconnect current source CS8b has an input that is coupled to receive an enable signal from the output of second interconnect AND gate 806. In one embodiment, the first interconnect current source CS8a can be replaced by a metal/oxide/silicon (MOS) transistor or a bipolar transistor acting as a switch. An interconnect node N8, which is between interconnect diode D8 and second interconnect current source CS8b, is coupled to interconnect-to-bus pin INT_UNIT. A first interconnect resistor R8a is coupled in series with an interconnect NFET M8 between the interconnect-to-bus pin INT_UNIT and the ground plane. A second interconnect resistor R8b is coupled between the interconnect-to-bus pin INT_UNIT and the ground plane. When interconnect NFET M8 is turned on, the first interconnect resistor R8a, which in one embodiment has a resistance of 100 kΩ, pulls down the bus to prevent leakage from causing a false alarm. Second interconnect resistor R8b, which in one embodiment has a resistance of 35 MΩ, prevents the interconnect-to-bus pin INT_UNIT from floating.

A hysteretic comparator 808 has a non-inverting input coupled to the interconnect node N8, an inverting input, an enable input, and an output. An interconnect voltage source VS8 is coupled between the inverting input of hysteretic comparator 808 and the ground plane. The interconnect voltage source VS8 provides interconnect comparator hysteresis and has an input coupled to an interconnect comparator hysteresis bit INT_HYS. In one embodiment, a value of zero on the interconnect comparator hysteresis bit causes the hysteretic comparator 808 to have 1.1 V hysteresis, and a value of one on the interconnect comparator hysteresis bit causes the hysteretic comparator 808 to have 0.1 V hysteresis.

Digital deglitch circuit 810 has a first input coupled to the output of hysteretic comparator 808, a second input coupled to interconnect deglitch bits INT_DEG, and an output that is coupled to a bit on a status register STATUS1. Interconnect deglitch bits INT_DEG allow the digital deglitch circuit 810 to be programed from 0 ms to 20 ms. An interconnect OR gate 812 has a first input coupled to the output of digital deglitch circuit 810, a second input, and an output coupled to the interconnect-to-MCU pin INT_MCU through an interconnect switch S8. A third interconnect AND gate 814 has a first input coupled to an interrupt signal INTERRUPT, a second input coupled to a status interrupt bit STATUS_INT, and an output coupled to the second input of interrupt OR gate 812. A fourth interconnect AND gate 816 has a first input coupled to the interconnect enable bit INT_EN, a second input coupled to the interconnect direction bit INT_DIR, and an inverted output coupled to control interconnect switch S8. A fifth interconnect AND gate 818 has a first input coupled to the interconnect enable bit INT_EN, a second input coupled to an inverse of the interconnect direction bit INT_DIR, and an output coupled to the enable input of hysteretic comparator 808.

Interconnect driver/receiver circuit 800 is active in mains-wired residential smoke alarm systems, where multiple smoke detection devices can communicate with each other using the wired interconnect bus 802 and a respective interconnect-to-bus pin INT_UNIT. This capability allows all of the smoke detection devices in a residence to sound an alarm simultaneously. An interconnect driver circuit, which includes first interconnect AND gate 804, second interconnect AND gate 806, first interconnect current source CS8a, and second interconnect current source CS8b, pulls the bus high when smoke is detected and low when smoke is cleared. The driver is current limited to handle short circuit conditions and has diode D8 on the high side driver to prevent the bus from driving voltage to boost pin VBST. The hysteretic comparator 808 senses when the bus is pulled high, filters the signal with digital deglitch circuit 810, and outputs the result to the interconnect-to-MCU pin INT_MCU and to the status register STATUS1. The interconnect-to-MCU pin INT_MCU has the additional function to output status interrupt signals. The status interrupt bit STATUS_INT enables interrupt signals to be output through the interconnect-to-MCU pin INT_MCU. However, when the interconnect driver circuit is enabled, the interrupt signal output is disconnected to allow the microcontroller to drive the interconnect-to-MCU pin INT_MCU.

Looking back at FIG. 1, residential smoke detection device 100 provides a horn driver circuit 146 that can be used to drive a piezoelectric horn 148, also called a piezo horn, which has either two terminals or three terminals. Selection of the type of piezo horn to be driven by SoC 108 is made using a horn selection bit HORN_SEL that can be set to zero for two terminals or one for three terminals. A three-terminal piezo horn receives feedback from a feedback electrode on the piezo horn and can be optimized for loudness using the feedback signal. In contrast, a two-terminal piezo horn relies on a signal from the MCU chip 102 for the speed at which the horn is driven.

Figure 9A:
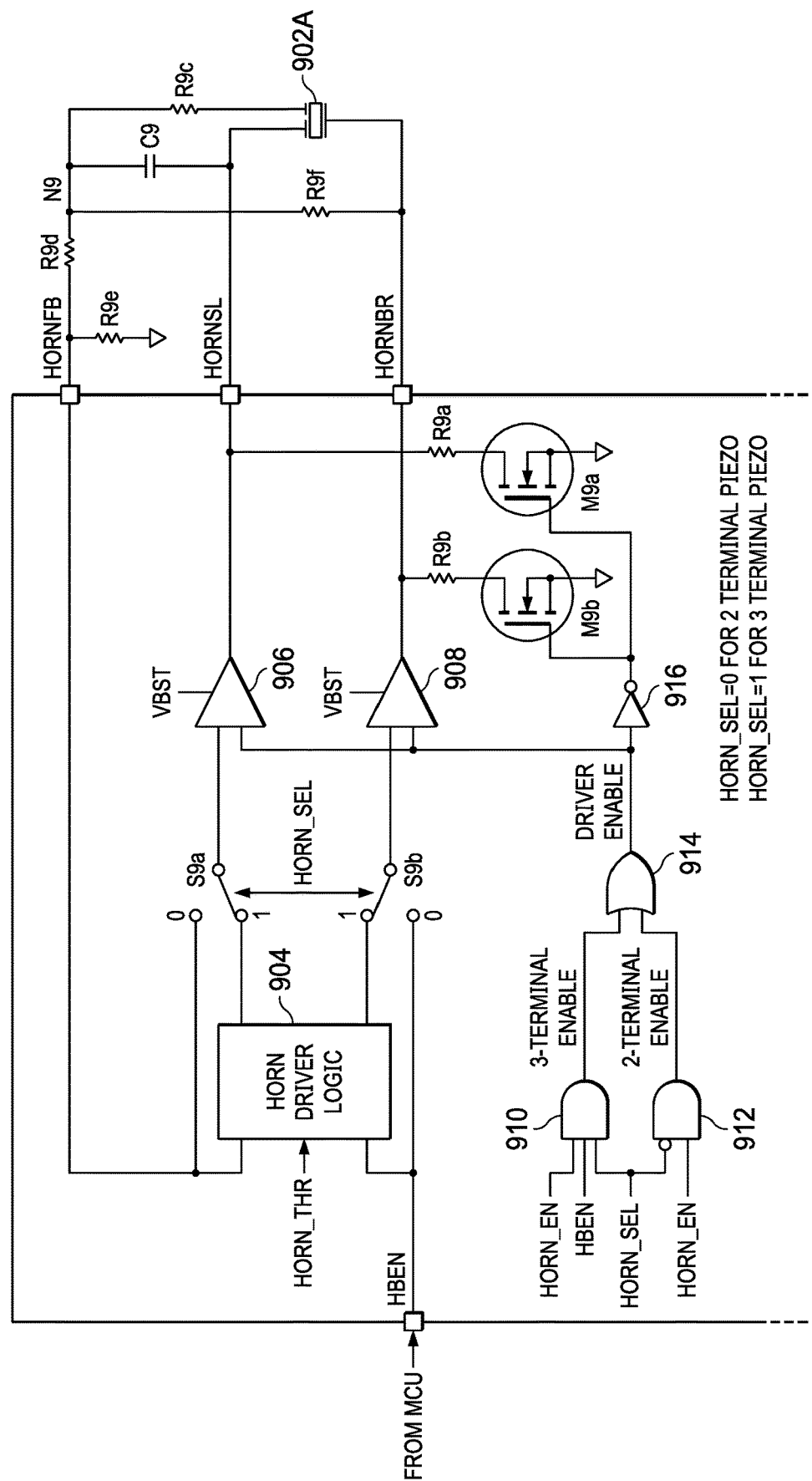
FIG. 9A depicts a three-terminal piezoelectric horn driver circuit that can be used in the smoke detection device of FIG. 1 according to an embodiment of the disclosure.

FIG. 9A depicts a piezo horn driver circuit 900A that is configured for a three-terminal piezo horn and an attached piezo horn 902A. Piezo horn driver circuit 900A includes horn driver logic 904 having a first horn driver input coupled to a horn feedback pin HORNFB, a second horn driver input coupled to horn threshold bits HORN_THR, a third horn driver input coupled to a horn block enable pin HBEN, a first horn driver output coupled to horn silver terminal pin HORNSL, and a second horn driver output coupled to horn brass terminal pin HORNBR. A first horn amplifier 906 has a first input, a second input and an output coupled to the horn silver terminal pin HORNSL; a second horn amplifier 908 has a first input, a second input and an output coupled to the horn brass terminal pin HORNBR. A first horn switch S9a is set by the horn selection bit HORN_SEL to couple the first input of first horn amplifier 906 to the first output of horn driver logic 904 and a second horn switch S9b is set by the horn selection bit HORN_SEL to couple the first input of second horn amplifier 908 to the second output of horn driver logic 904. A first horn resistor R9a is coupled in series with a first horn NFET M9a between the horn silver terminal pin HORNSL and the ground plane; a second horn resistor R9b is coupled in series with a second horn NFET M9b between the horn brass terminal pin HORNBR and the ground plane. A first horn AND gate 910 has a first input coupled to receive a horn enable bit HORN_EN, a second input coupled to the horn block enable pin HBEN, a third input coupled to the horn selection bit HORN_SEL, and an output that provides a three-terminal enable signal. A second horn AND gate 912 has a first input coupled to receive an inverse of the horn selection bit HORN_SEL, a second input coupled to the horn enable bit HORN_EN, and an output that provides a two-terminal enable signal. A horn OR gate 914 has a first input coupled to the output of first horn AND gate 910, a second input coupled to the output of second horn AND gate 912, and an output that is coupled to the second input of first horn amplifier 906 and the second input of second horn amplifier 908 as a driver enable signal. An inverter 916 has an input coupled to the output of the horn OR gate 914 and an output coupled to the gate of first horn NFET M9a and second horn NFET M9b.

In the three-terminal mode, the silver terminal and the brass terminal of the piezo horn 902A are coupled directly to the horn silver terminal pin HORNSL and the horn brass terminal pin HORNBR respectively. A third horn resistor R9c is coupled in series with a fourth horn resistor R9d between the feedback terminal of the piezo horn 902A and the horn feedback pin HORNFB. A fifth horn resistor R9e is coupled between the horn feedback pin HORNFB and the ground plane; a sixth horn resistor R9f is coupled between the horn brass terminal pin HORNBR and a horn node N9, which lies between the third horn resistor R9c and the fourth horn resistor R9d; and a horn capacitor C9 is coupled between the horn node N9 and the horn silver terminal pin HORNSL.

During operation, the piezo horn driver circuit 900A is enabled and begins oscillating when the horn enable register bit HORN_EN and the horn block enable pin HBEN are set high. The value of the resistor connected to the piezo feedback terminal can be adjusted to tune the oscillation frequency. Trial and error is generally necessary to select this resistance. After the driver achieves resonant oscillation, the duty cycle of the outputs of the horn silver terminal pin HORNSL and the horn brass terminal pin HORNBR can be adjusted through the MCU chip 102 using the horn threshold bits HORN_THR to maximize the loudness.

Figure 9B:
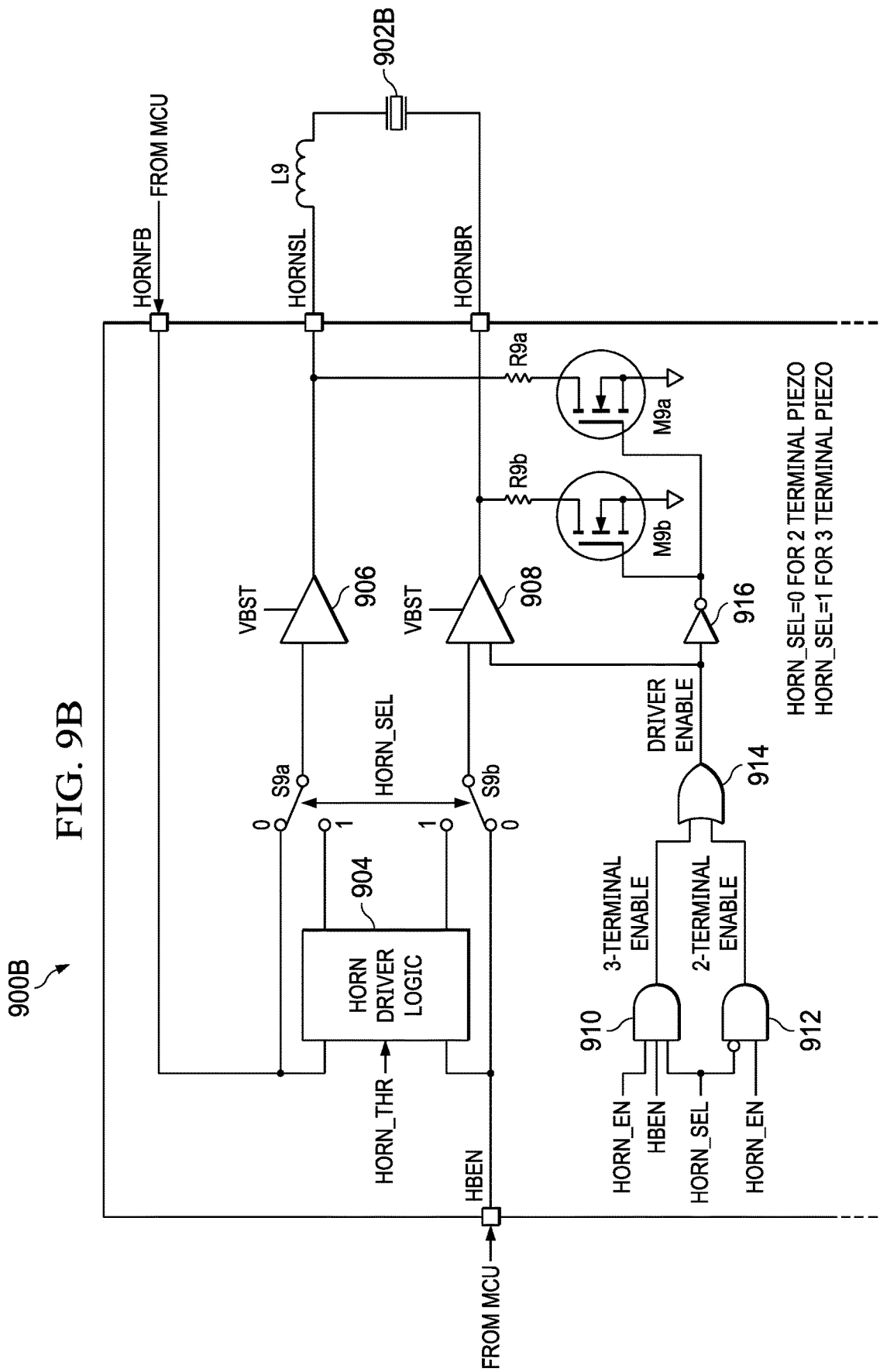
FIG. 9B depicts a two-terminal piezoelectric horn driver circuit that can be used in the smoke detection device of FIG. 1 according to an embodiment of the disclosure.

FIG. 9B depicts a piezo horn driver circuit 900B that is configured for a two-terminal piezo horn and an attached piezo horn 902B. Internal to piezo horn driver circuit 900B, the value of horn selection bit HORN_SEL has changed, so that first horn switch S9a couples the first input of first horn amplifier 906 to the horn feedback pin HORNFB and the second horn switch S9b couples the first input of second horn amplifier 908 to the horn block enable pin HBEN. In this configuration, both the horn feedback pin HORNFB and the horn block enable pin HBEN are controlled by the MCU, e.g. MCU chip 102, ensuring that the output of the first horn amplifier 906 and the output of the second horn amplifier 908 are controlled directly by signals from MCU chip 102. External to piezo horn driver circuit 900B, piezo horn 902b requires only that the brass terminal be coupled to the horn brass terminal pin HORNBR and that the silver terminal be coupled to the horn silver terminal pin HORNSL through a horn inductor L9, which in one embodiment has an inductance of 1 mH. The MCU chip 102 sends an arbitrary pulse width modulated (PWM) signal to control the driving voltages to the piezo horn. The PWM signal can be a square wave of the oscillation frequency, a sine wave of the oscillation frequency, or an arbitrary shape for voice applications. The horn inductor L9 serves to improve the rise time and fall time of the output and reduces power dissipation.

While residential smoke detection devices use the interconnect driver/receiver circuit 800 for communication between devices in the same residence and use a piezo horn 902x and a piezo horn driver circuit 900x to sound an alarm, commercial smoke detection devices use neither of these. Instead, an FACP in a commercial smoke detection system provides an SLC for communication with all the devices in a "zone". Devices coupled to the SLC can include smoke detection devices, heat detectors, manual call points, warning system/bells, control modules, relay modules, etc.

The SLC provides the power for all of the fire detection devices, such as smoke detection device 100, which are coupled on the SLC. The SLC also carries data sent from the FACP to the fire detection devices, e.g., address and polling information, and data sent from the fire detection devices to the FACP, e.g., address, polling acknowledgements, alarm, supervisory, and trouble signals.

Figure 10:
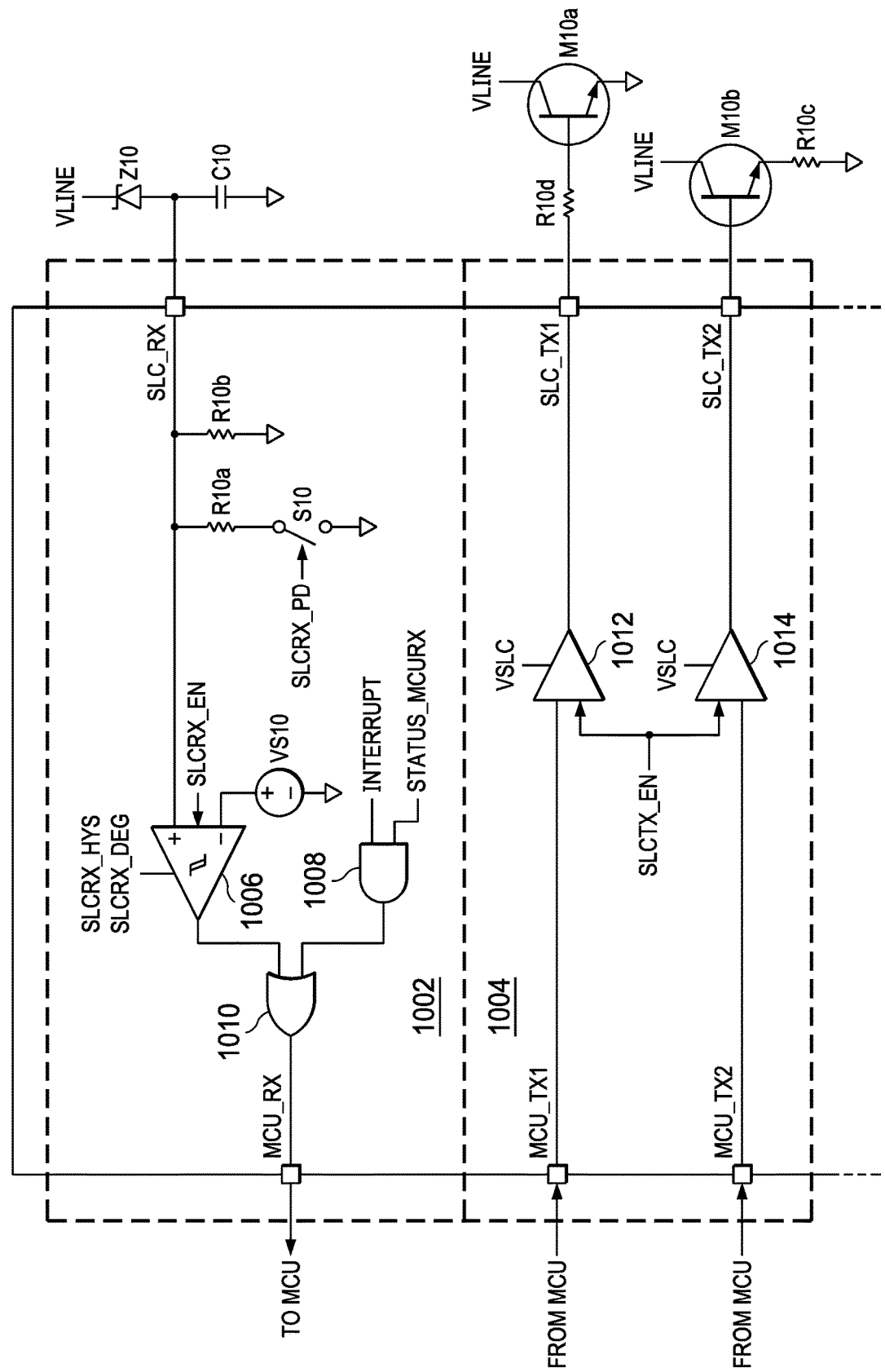
FIG. 10 depicts an signaling line circuit that can be used in the smoke detection device of FIG. 1 according to an embodiment of the disclosure.

FIG. 10 depicts a signaling line circuit 1000 according to an embodiment of the disclosure. The external component selection shown is only one example, as different components can be used with other specific SLC protocols, which can vary by provider. The signaling line circuit 1000 is not specifically shown in FIG. 1 because the SLC is not a totally separate circuit with dedicated pins, as with, for example, the sensor drivers. Instead, signaling line circuit 1000 is integrated with other circuits and repurposes horn feedback pin HORNFB, horn brass terminal pin HORNBR, horn silver terminal pin HORNSL, horn block enable pin HBEN, interconnect-to-MCU pin INT_MCU, and interconnect-to-bus pin INT_UNIT. The repurposed pins are relabeled in signaling line circuit 1000. The signaling line circuit 1000 connects to the power line VLINE to transmit and receive data from the MCU chip 102. At the same time, although not specifically shown, the power line VLINE is also coupled to the trace T1 to receive power. The SLC isolates the high voltage power line from the MCU chip 102, mitigates risk of damage, and reduces the external component count.

Signaling line circuit 1000 includes an SLC receive circuit 1002 and an SLC transmit circuit 1004. SLC receive circuit 1002 includes SLC comparator 1006, SLC AND gate 1008, SLC OR gate 1010, voltage source VS10, first SLC resistor R10a, second SLC resistor R10b, and SLC switch S10. SLC comparator 1006 has a non-inverting input, an inverting input, an output, a first control input coupled to an SLC receiver comparator hysteresis bit SLCRX_HYS, and a second control input coupled to SLC receiver deglitch bits SLCRX_DEG. The non-inverting input of SLC comparator 1006 is coupled to an SLC receive pin SLC_RX; the first SLC resistor R10a is coupled in series with SLC switch S10 between the SLC receive pin SLC_RX and the ground plane; and the second SLC resistor R10b is coupled between the SLC receive pin SLC_RX and the ground plane. SLC switch S10 is controlled by an SLC pulldown resistor enable bit SLCRX_PD. Voltage source VS10 is coupled between the inverting input of SLC comparator 1006 and the ground plane. SLC AND gate 1008 has a first input that is coupled to an interrupt signal INTERRUPT, a second input that is coupled to a status interrupt on the MCU_RX pin bit STATUS_MCURX, and an output. SLC OR gate 1010 has a first input coupled to the output of SLC comparator 1006, a second input coupled to the output of SLC AND gate 1008, and an output coupled to the MCU receive pin MCU_RX. External to signaling line circuit 1000, a power line VLINE is coupled through a Zener diode Z10 to the SLC receive pin SLC_RX, with an SLC capacitor C10 also coupled to the SLC receive pin SLC_RX.

When operating, the SLC receiver (not specifically shown) transmits signals on the power line VLINE to the MCU chip 102. The SLC Zener diode Z10, which is reverse biased, level shifts the power line and is selected to drop the voltage such that when power line VLINE is high, the SLC receive pin SLC_RX is above 3 V and when power line VLINE is low, the SLC receive pin SLC_RX is below 0.5 V. The SLC capacitor, which in one embodiment is 100-pF, filters voltage spikes that may occur on power line VLINE. The hysteretic and deglitched comparator filters spurious noise on power line VLINE. The output of SLC comparator 1006 is synchronized with a 32 kHz clock before being deglitched. The hysteresis voltage and deglitch time are programmable with the SLC receiver comparator hysteresis bit SLCRX_HYS and with the SLC receiver deglitch bits SLCRX_DEG. Second SLC resistor R10b is an internal pulldown resistor that biases the SLC Zener diode Z10 to maintain the voltage on SLC receive pin SLC_RX below 17 V, which is the recommended maximum.

SLC transmit circuit 1004 includes a first SLC amplifier 1012 having an input coupled to a first MCU transmit pin MCU_TX1, an output coupled to a first SLC transmit pin SLC_TX1, and an enable input coupled to receive an SLC transmit enable bit SLCTX_EN. SLC transmit circuit 1004 also includes a second SLC amplifier 1014 having an input coupled to a second MCU transmit pin MCU_TX2, an output coupled to a second SLC transmit pin SLC_TX2, and an enable input coupled to receive the SLC transmit enable bit SLCTX_EN. Externally, a first SLC NPN M10a is coupled between power line VLINE and the ground plane and a second SLC NPN M10b is coupled between power line VLINE and the ground plane. The third SLC resistor R10c is coupled between the emitter of second SLC NPN M10b and the ground plane. A fourth SLC resistor R10d is coupled between the first SLC transmit pin SLC_TX1 and the base of the first SLC NPN M10a and the second SLC transmit pin SLC_TX2 is coupled to the base of second SLC NPN M10b.

The MCU chip 102 transmits signals to the power line VLINE by pulling the power line VLINE low with a controlled current sink. When the SLC transmit circuit is enabled, the microcontroller controls the outputs from first SLC transmit pin SLC_TX1 and from second SLC transmit pin SLC_TX2 by driving first MCU transmit pin MCU_TX1 and second MCU transmit pin MCU_TX2 high. In signaling line circuit 1000, the second SLC NPN M10b is coupled to the current-limiting third SLC resistor R10c and draws a limited current from the power line VLINE. The first SLC NFET M10a is able to pull the power line VLINE completely low. This configuration allows multi-level communication.

One advantage to the integration of multiple circuits into an SoC is that providing error messages or communications to the MCU chip 102 can also be integrated. These interrupt signals are individually configurable to notify the MCU chip 102 when a system anomaly occurs. The interrupt signals are stored in the STATUS1 register, which has bits that latch high when various condition limits are reached, e.g., temperature or voltage. Each of the STATUS1 register bits can be independently configured to send an interrupt signal by setting the corresponding MASK register bit. Bits in the general purpose I/O register GPIO[0:2] can be set to output interrupt signals through the general purpose I/O pin GPIO, and the STATUS_INT bit can be set to output interrupt signals through the interconnect-to-MCU pin INT_MCU or through MCU receive pin MCU_RX. By connecting any of the general purpose I/O pin GPIO, interconnect-to-MCU pin INT_MCU, and the MCU receive pin MCU_RX to the microcontroller, the MCU chip 102 can be immediately notified when a STATUS1 bit changes instead of having to repeatedly read the STATUS1 register. After the SoC 108 sends the interrupt signal, the signal remains high until the STATUS1 register is read by the MCU chip 102, at which point the fault clears if the error condition is removed.

Figure 11:
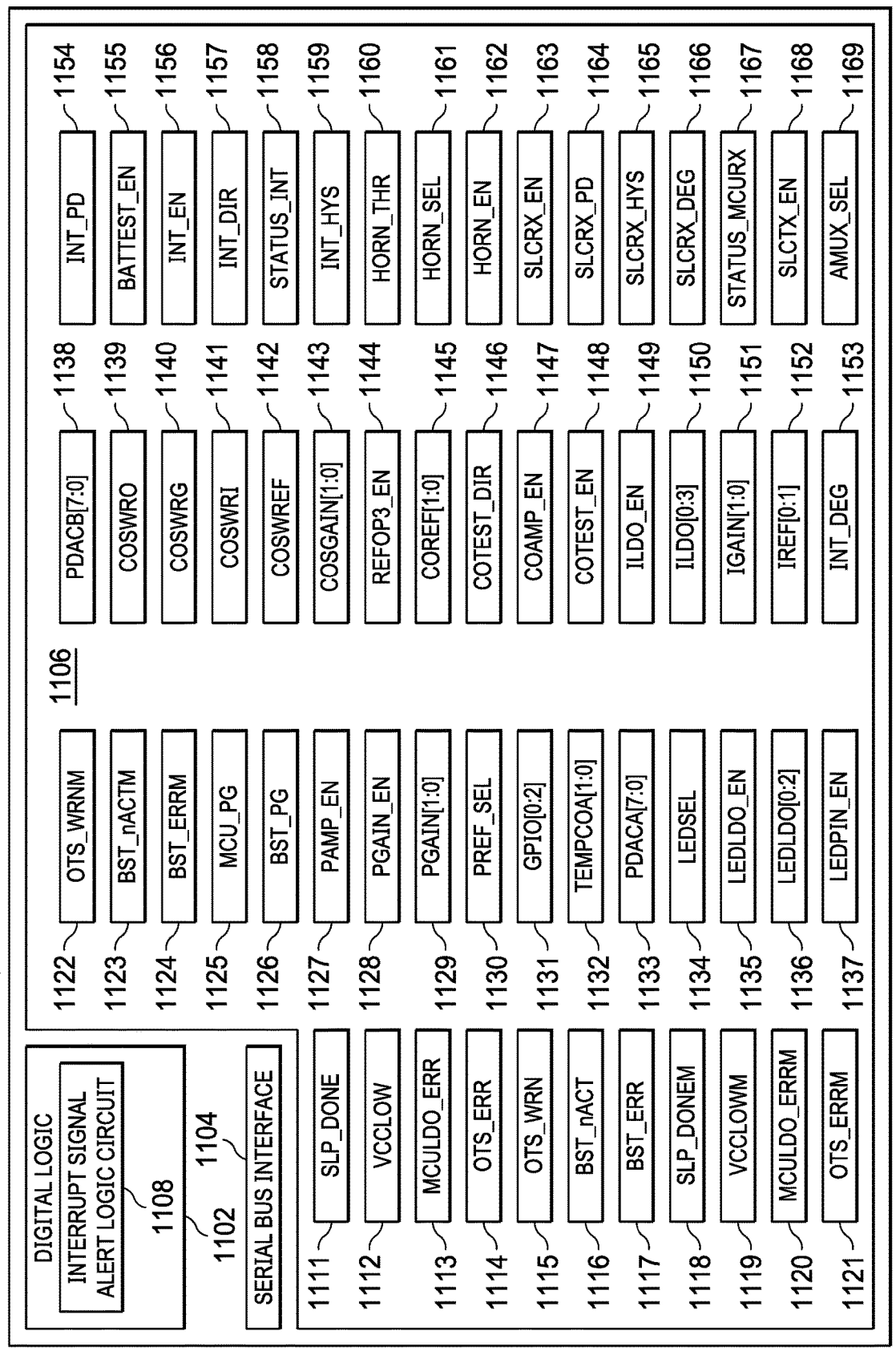
FIG. 11 depicts a digital core that can be used in the smoke detection device of FIG. 1 according to an embodiment of the disclosure.

FIG. 11 depicts a digital core 1100 according to an embodiment of the disclosure. The digital core 1100 includes a digital logic circuit 1102, a serial bus interface 1104 and register bits 1106. Digital logic circuit 1102 includes an interrupt signal alert logic circuit 1108 that will be discussed in further detail below. Although register bits 1106 is shown as containing numerous individual indicators, the register bits, which may be single bit indicators or contain a greater number of bits, can be grouped into larger registers as desired. The following description is given to provide an idea of the versatility that can be incorporated into the disclosed SoC when multiple capabilities are integrated into a single chip. Other indicators that are not specifically shown here can also be included. While some of the indicators are explained in absolute terms, e.g., whether or not power at a specific point is as expected, there may be other conditions that modify the action of specific indicators, e.g., the indicator is not active during a sleep mode.

A number of register bits 1106, e.g., bits that are part of the STATUS1 register, are used to signal the presence of specific conditions that may affect or need to be reported to the MCU. When smoke detection device 100 is operating on a low-voltage battery, e.g., a 3-volt battery, the SoC 108 can place itself into a sleep mode to save power. A sleep timer wakeup flag SLP_DONE 1111 can be used to signal when the period for sleep is over and the SoC 108 and the MCU chip 102 can be activated. A VCC low warning flag VCCLOW 1112 is set when the power at the pre-LDO input pin VCC falls below a selectable falling value V_VCCLOW, FALL (not specifically shown). An MCU LDO power good error flag MCULDO_ERR 1113 is set to indicate that an error has occurred with the power at the MCU LDO output. A thermal shutdown error flag OTS_ERR 1114 indicates that the junction temperature has exceeded a selectable shutdown temperature T_SHUTDOWN (not specifically shown), while a thermal warning flag OTS_WRN 1115 indicates that the junction temperature has exceeded a warning value T_WARNING (not specifically shown). A boost activity monitor flag BST_nACT 1116 is used to indicate whether the DC/DC boost converter 702 is actively switching or has not switched for a selectable boost inactive time T_BST, ACT (not specifically shown) and a boost converter power good error flag BST_ERR 1117 indicates that an error has occurred on the DC/DC boost converter 702.

Each of the above conditions can be used and/or reported to the MCU chip 102 by SoC 108 if desired; a respective mask is available for each flag, so that a user can indicate whether or not each reporting flag should be utilized. These masks include a sleep timer wakeup flag mask SLP_DO-NEM 1118, a VCC low warning flag mask VCCLOWM 1119, an MCU LDO power good error flag mask MCUL-DO_ERRM 1120, a thermal shutdown error flag mask OTS_ERRM 1121, a thermal warning flag mask OTS_WRNM 1122, a boost activity monitor flag mask BST_nACTM 1123, and a boost converter power good error flag mask BST_ERRM 1124. Use of the flags and respective masks is discussed in FIG. 12 below. A general purpose I/O indicator 1131 can be used to output interrupt signals through the GPIO pin.

An MCU LDO power good indicator MCU_PG 1125 indicates whether the power at the MCU LDO is above or below a power good threshold and a boost power good indicator BST_PG 1126 indicates whether the power at the DC/DC boost converter output is above or below a power good threshold. Many indicators are used to provide control or changes in the analog modules, e.g., the CO amplifier circuit 110, the photoelectric amplifier circuit 112, and the ionization amplifier circuit 118.

With references back to photoelectric amplifier circuit 200, a photo input amplifier control bit PAMP_EN 1127 can enable or disable the photo input amplifier 204; a photo gain amplifier control bit PGAIN_EN 1128 can enable or disable the photo gain amplifier 206; and a photo gain register PGAIN[1:0] 1129 can be used to set the gain by adjusting the resistance at first photo resistor R2a. A photo reference setting PREF_SEL 1130 determines whether photo reference or terminal PREF is coupled to ground or to a 50 mV internal reference CS2b.

With reference back to LED driver circuit 300, first temperature coefficient bits TEMPCOA[1:0] 1132 and second temperature coefficient bits TEMPCOB[1:0] (not specifically shown) are used to set the temperature coefficient for the LED driver circuit 300 and are used in conjunction with first current setting register PDACA[7:0] 1133 and second current setting register PDACB[7:0] 1138 to control the current provided to first LED NFET M3a and second LED NFET M3b. The LED selection bit LEDSEL 1134 controls the driver to which the signal on LED enable pin LEDEN is connected. An LED LDO enable bit LEDL-DO_EN 1135 can enable or disable the LED LDO regulator circuit 302; LED LDO register LEDLDO[0:2] 1136 can be used to adjust the regulation voltage in the LED LDO regulator circuit 302; and an LED pin enable bit LEDPI-N_EN 1137 can configure whether or not the LED enable pin LEDEN will enable the LED block. In an embodiment in which the ion LDO regulator circuit 510 and LED LDO regulator circuit 302 are the same circuit, it can be recognized that control bits for the LED LDO regulator circuit 302 are also controls bits for the ion LDO regulator circuit 510.

With reference back to CO amplifier circuit 400, a CO amplifier output resistor enable bit COSWRO 1139 can be used to enable or disable the CO output switch S4a; a CO gain resistor enable bit COSWRG 1140 can be used to enable or disable the CO feedback switch S4b, a CO input resistor enable bit COSWRI 1141 can be used to enable or disable the first CO input resistor S4c, a CO reference switch enable bit COSWREF 1142 can be used to enable or disable the second CO input switch S4d, a CO feedback resistance setting COSGAIN[1:0] 1143 can be used to adjust the resistor on CO gain resistor R4c; and a 300 mV reference enable REFOP3_EN 1144 can be used to enable a 300 mV reference voltage (not specifically shown). A CO amplifier reference voltage COREF[1:0] 1145 can be used to set the voltage output by CO voltage source VS4; the CO test output direction bit COTEST_DIR 1146 indicates whether the CO test output is pulldown or pullup; the CO amplifier enable bit COAMP_EN 1147 can enable or disable CO transimpedance amplifier 402; and a CO test output enable bit COTEST_EN 1148 can enable or disable CO test output on photo reference pin PREF.

Next, with reference back to ionization amplifier circuit 500, the ion LDO enable bit ILDO_EN 1149 can be used to enable or disable the ion LDO regulator circuit 510 and the ion LDO setting ILDO[0:3] 1150 can be used to set a voltage for the ion LDO regulator circuit 510. The ion gain setting register IGAIN[1:0] 1151 can be used to set the gain for ion gain amplifier 506; the ion reference voltage settings IREF [0:1] 1152 can be used to set the reference voltage on the ion voltage source VS5.

With reference next to the interconnect driver/receiver circuit 800, interconnect deglitch bits INT_DEG 1153 can be used to program the digital deglitch circuit 810 between 0 ms and 20 ms. An interconnect unit pulldown resistor enable INT_PD 1154 can be used to enable the interconnect NFET M8; the interconnect enable bit INT_EN 1156 can be used to enable or disable the interconnect driver/receiver circuit 800; the interconnect direction bit INT_DIR 1157 can be used to indicate the direction of communication on the interconnect driver/receiver circuit 800. The status interrupt bit STATUS_INT 1158 can be used to provide interrupts to the MCU through the interconnect-to-MCU pin INT_MCU; and interconnect comparator hysteresis bit INT_HYS 1159 can be used to indicate the amount of voltage hysteresis on the third interconnect voltage source VS8.

With reference to the horn driver circuit 146, the horn threshold bits HORN_THR 1160 can be used to provide duty cycle tuning for the piezoelectric horn 148 in three-terminal operations. The horn selection bit HORN_SEL 1161 can be used to designate that the horn is a two-terminal or a three-terminal piezoelectric horn; while the horn enable bit HORN_EN 1162 can be used to enable the horn driver circuit 146.

Referring next to signaling line circuit 1000, the SLC receiver enable bit SLCRX_EN 1163 can be used to enable or disable the SLC receive circuit 1002; the SLC pulldown resistor enable bit SLCRX_PD 1164 can be used to enable the pulldown resistor by closing SLC switch S10; and the SLC receiver comparator hysteresis bit SLCRX_HYS 1165 can be used to designate the hysteresis voltage on SLC comparator 1006. The status interrupt on the MCU receive pin bit STATUS_MCURX 1167 can be set to designate that interrupt signals be output through the MCU receive pin MCU_RX and the SLC transmit enable bit SLCTX_EN 1168 can be set to enable the SLC transmit circuit 1004. Because, as was mentioned in discussion of the signaling line circuit 1000, the signaling line circuit 1000 is integrated with other circuits, e.g., the piezo horn driver circuit 900 and the interconnect driver/receiver circuit 800, only one of the signaling line circuit 1000 and the interconnect driver/receiver circuit 800 will be active and providing communication with the MCU in any specific instance of the smoke detection device.

Finally, a battery test enable bit BATTEST_EN 1155 enables or disables a battery test using battery test circuit 150 in smoke detection device 100 and analog MUX selection bits AMUX_SEL[1:0] can be used to designate an input to the analog multiplexor circuit 600 that is to be passed to the MCU.

By providing all of these control inputs and error flags on a single chip with the circuits that they control, the MCU is able to easily change parameters for the analog circuits on the fly and can monitor and respond to circumstances in a manner that either is not possible with previous circuits or else was more difficult to implement.

Figure 12:
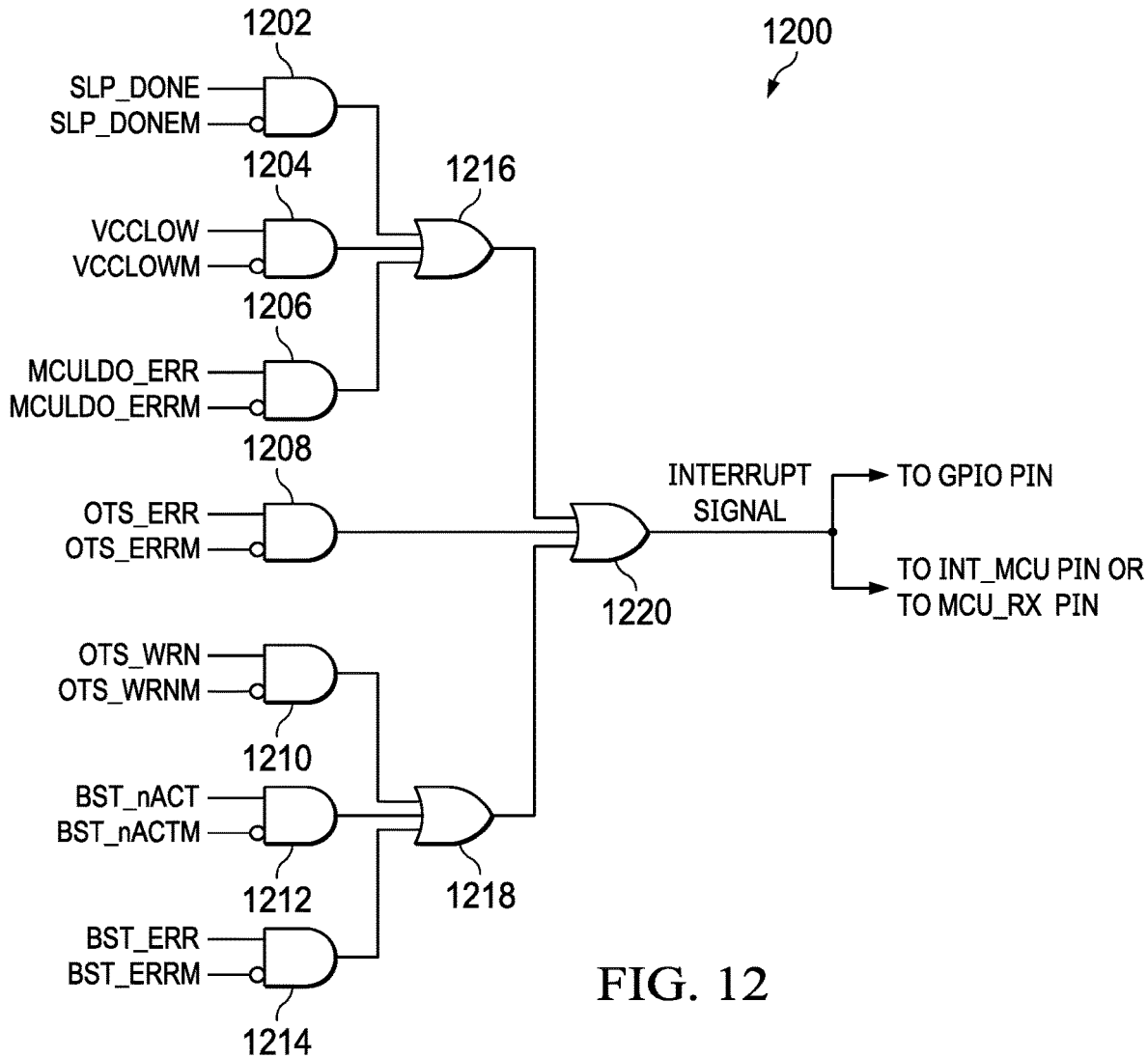
FIG. 12 depicts interrupt signal alert logic according to an embodiment of the disclosure.

FIG. 12 depicts an interrupt signal alert logic circuit 1200 that uses some of the flags and masks stored in the register bits 1106 according to an embodiment of the disclosure. The interrupt signal alert logic circuit 1200 includes a number of interrupt AND gates, each of which inputs both a given flag bit and the corresponding mask bit, and a number of interrupt OR gates that combine the individual AND gate outputs. A first interrupt AND gate 1202 has a first interrupt input coupled to a sleep timer wakeup flag SLP_DONE, a second interrupt input coupled to an inverse of a sleep timer wakeup interrupt mask SLP_DONEM, and an interrupt output; a second interrupt AND gate 1204 has a first interrupt input coupled to a VCC low warning flag VCCLOW, a second interrupt input coupled to an inverse of a VCC low warning interrupt mask VCCLOWM, and an interrupt output; a third interrupt AND gate 1206 has a first interrupt input coupled to an MCU LDO power good error flag MCULDO_ERR, a second interrupt input coupled to an inverse of an MCU LDO power good error interrupt mask MCULDO_ERRM, and an interrupt output; a fourth interrupt AND gate 1208 has a first interrupt input coupled to a thermal shutdown error flag OTS_ERR, a second interrupt input coupled to an inverse of a thermal shutdown error interrupt mask OTS_ERRM, and an interrupt output; fifth interrupt AND gate 1210 has a first interrupt input coupled to a thermal warning flag OTS_WRN, a second interrupt input coupled to an inverse of thermal warning interrupt mask OTS_WRNM, and an interrupt output; a sixth interrupt AND gate 1212 has a first interrupt input coupled to a boost activity monitor flag BST_nACT, a second interrupt input coupled to an inverse of a boost activity monitor interrupt mask BST_nACTM, and an interrupt output; and a seventh interrupt AND gate 1214 has a first interrupt input coupled to a boost converter power good error flag BST_ERR, a second interrupt input coupled to an inverse of a boost converter power good interrupt mask BST_ERRM, and an interrupt output.

A first interrupt OR gate 1216 has a first interrupt input coupled to the interrupt output of first interrupt AND gate 1202, a second interrupt input coupled to the interrupt output of second interrupt AND gate 1204, a third interrupt input coupled to the interrupt output of third interrupt AND gate 1206, and an interrupt output. Similarly, second interrupt OR gate 1218 has a first interrupt input coupled to the output of fifth interrupt AND gate 1210, a second interrupt input coupled to the output of sixth interrupt AND gate 1212, a third interrupt input coupled to the interrupt output of seventh interrupt AND gate 1214, and an interrupt output. Third interrupt OR gate 1220 has a first interrupt input coupled to the interrupt output of first interrupt OR gate 1216, a second interrupt input coupled to the interrupt output of fourth interrupt AND gate 1208, a third interrupt input coupled to the interrupt output of second interrupt OR gate 1218 and an interrupt output that is selectively coupled to any of the general purpose I/O pin GPIO, the interconnect-to-MCU pin INT_MCU, and the MCU receive pin MCU_RX. It will be understood that while the interrupt process has been shown to be implemented by specific logic gates, other arrangements of logic gates can be used to achieve the same results.

Figure 13:
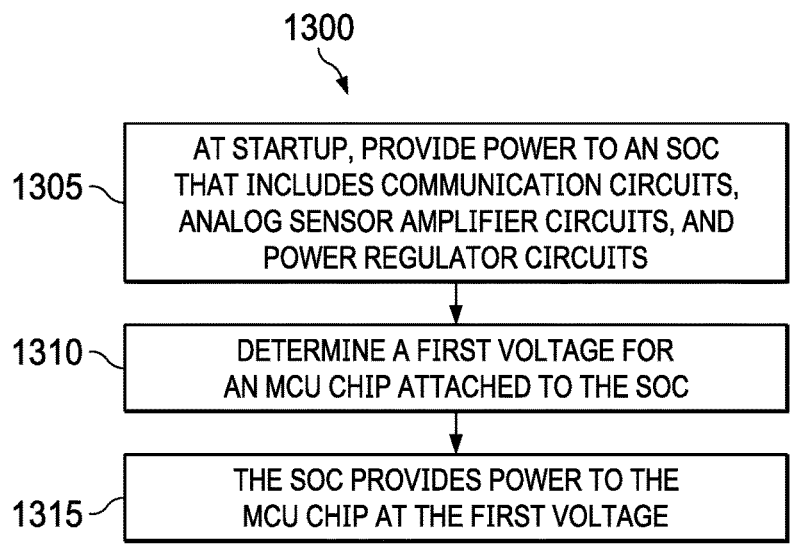
FIG. 13 depicts a process of operating a smoke detection device according to an embodiment of the disclosure.

FIG. 13 depicts a method 1300 of operating a smoke detection device according to an embodiment of the disclosure and FIGS. 13A-13E depict possible additions to the method 1300. Method 1300 includes, at startup, providing 1305 power to an SoC that includes communication circuits, analog sensor amplifier circuits, and power regulator circuits. The SoC determines 1310 a first voltage for an MCU chip that is attached to the SoC. This determination can be made, e.g., depending on what is attached to a given pin on the SoC. The SoC then provides 1315 power to the MCU chip at the first voltage.

Figure 13A:
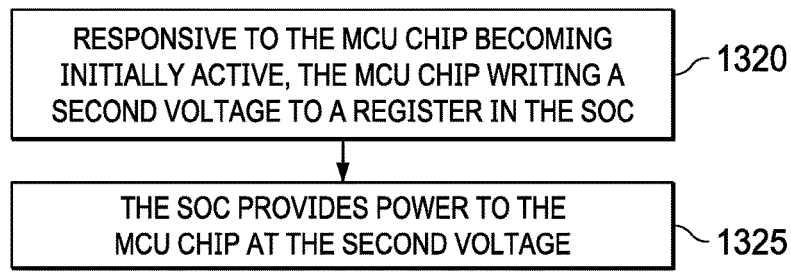
Figure 13B:
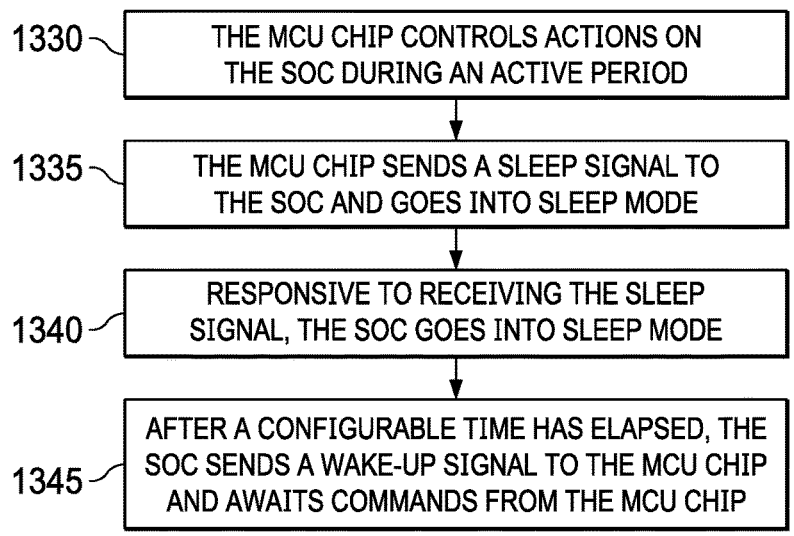

In FIG. 13A, method 1300 may continue, responsive to the MCU chip becoming initially active, the MCU chip writing 1320 a second voltage to a register in the SoC. Thereafter, the SoC provides 1325 power to the MCU chip at the second voltage. In FIG. 13B, the MCU chip controls 1330 actions on the SoC during an active period. At some point, the MCU chip sends 1335 a sleep signal to the SoC and goes into a sleep mode. Responsive to receiving the sleep signal, the SoC goes 1340 into sleep mode. After a configurable time has elapse, the SoC sends 1345 a wake-up signal to the MCU chip and awaits commands from the MCU chip. In one embodiment, the configurable time is between 1 millisecond and 65 seconds inclusive.

In FIG. 13C, a DC/DC boost converter of the power regulator circuits is configured 1350 to be either disabled or unchanged in sleep mode. The analog sensor amplifier circuits are configured 1355 to be either disabled or unchanged in sleep mode and an MCU LDO regulator of the power regulator circuits is also configured 1360 to be either disabled or unchanged in sleep mode. The ability to disable circuits within the SoC during sleep mode can be of great importance when the smoke detection device is operating on a low-voltage battery, but may be much less important when the smoke detection device is receiving power from higher-voltage sources such as mains power through an AC/DC converter or from a central alarm system through the power line VLINE.

In FIG. 13D, each of a signaling line circuit, an interconnect circuit, a horn driver circuit, a carbon monoxide amplifier circuit, and an ionization amplifier circuit are separately electronically configured 1365 as either active or disabled. This can configure the SoC for use in a particular type of smoke detection device. In FIG. 13E, the SoC detects 1370 an alert condition on the SoC and sends 1375 an interrupt to the MCU chip regarding the alert condition. As noted previously, the interrupt may be caused by conditions including but not limited to a boost regulator being under-voltage, an MCU-LDO output being under-voltage, a substrate of the SoC being over-temperature, an interconnection alert, and an SLC power alert. The interconnection alert can be any alert provided by the interconnect driver/receiver.

Applicants have disclosed a smoke detection device that utilizes only two ICs: an MCU and an SoC that incorporates power regulator circuits, sensor amplifiers, a horn driver circuit, and communication circuits that operate under the control of the MCU. The high degree of integration provides greater control of the individual blocks on the SoC, improved error detection, and greater power control. The disclosed smoke detection device and SoC provide all of the capabilities required by the 2020 UL regulations.

Although various embodiments have been shown and described in detail, the claims are not limited to any particular embodiment or example. None of the above Detailed Description should be read as implying that any particular component, element, step, act, or function is essential such that it must be included in the scope of the claims. Reference to an element in the singular is not intended to mean "one and only one" unless explicitly so stated, but rather "one or more." All structural and functional equivalents to the elements of the above-described embodiments that are known to those of ordinary skill in the art are expressly incorporated herein by reference and are intended to be encompassed by the present claims. Accordingly, those skilled in the art will recognize that the exemplary embodiments described herein can be practiced with various modifications and alterations within the spirit and scope of the claims appended below.

What is claimed is:

1. A system on a chip (SoC) for smoke detection, the SoC comprising:
    power regulator circuits coupled to power regulator terminals of the SoC;
    analog sensor amplifier circuits coupled to the power regulator circuits, the analog sensor amplifier circuits including a photoelectric amplifier circuit, a carbon monoxide amplifier circuit, and a light emitting diode driver circuit; and
    a digital core that includes a digital logic circuit, register bit flags, and a communication circuit, the communication circuit being coupled to a data terminal, the register bit flags being coupled to the power regulator circuits, the analog sensor amplifier circuits, and the communication circuit.

2. The SoC of claim 1 in which the register bit flags include status register bit flags and control register bit flags.

3. The SoC of claim 1 in which the register bit flags include one of a sleep timer wakeup flag, a VCC low warning flag, an MCU LDO power good error flag, a thermal shutdown error flag, a thermal warning flag, a boost activity monitor flag, and a boost converter power good error flag.

4. The SoC of claim 1 in which the register bit flags include register bit flag masks.

5. The SoC of claim 4 in which the digital logic includes an interrupt signal alert logic circuit, the interrupt signal alert logic circuit including:
    a first interrupt AND gate having a first interrupt input coupled to a first register bit flag, a second interrupt input coupled to a first register bit flag mask, and a first interrupt output,
    a second interrupt AND gate having a first interrupt input coupled to a second flag, a second interrupt input coupled to a second register bit flag mask, and a second interrupt output, and
    an OR gate having inputs coupled to the first interrupt output and the second interrupt output and having an OR interrupt output coupled to an interrupt output terminal.

6. The SoC as recited in claim 1 in which the communication circuit is an Inter-Integrated Circuit (I2C) interface coupled to a serial data terminal and having an input coupled to a serial clock terminal.

7. The SoC as recited in claim 1 including an interconnect driver receiver circuit having an input coupled to a register bit flag and being coupled to an interconnect-to-MCU terminal and an interconnect-to-unit terminal.

8. The SoC of claim 7 in which the interconnect driver receiver circuit includes:
    a hysteretic comparator having an input coupled to the interconnect-to-unit terminal and having a hysteretic output; and
    a deglitch circuit having an input coupled to the hysteretic output and having an output coupled to the interconnect-to-MCU terminal.

9. The SoC of claim 1 including a signaling line circuit coupled to an signaling line receive terminal, a first signaling line transmit terminal, a second signaling line transmit terminal, an MCU receive terminal, a first MCU transmit terminal, and a second MCU transmit terminal.

10. The SoC of claim 9 in which the signaling line circuit includes a comparator having an input coupled to the signaling line receive terminal and having an output coupled to the MCU receive terminal.

11. The SoC of claim 9 in which the signaling line circuit includes:
    a first transmit amplifier circuit having an input coupled to the first MCU transmit terminal, having in input coupled to a transmit enable register bit flag, and having an output coupled to the first signaling line transmit terminal; and
    a second transmit amplifier circuit having an input coupled to the second MCU transmit terminal, having in input coupled to the transmit enable register bit flag, and having an output coupled to the second signaling line transmit terminal.

12. The SoC of claim 1 including a horn driver circuit having a horn block enable input, having a feedback input coupled to a horn feedback terminal, having a first horn output coupled to a horn silver output terminal, and having a second horn output coupled to a horn brass output terminal.

13. The SoC of claim 1 including an analog multiplexer circuit having analog sensor inputs coupled to the analog sensor amplifiers and having an analog multiplexer output coupled to an analog multiplexer output terminal.

14. The SoC of claim 13 in which the analog sensor inputs include:
    an ION analog input;
    a carbon monoxide amplifier analog input;
    a photodiode output terminal input;
    a photo gain input; and
    register bit flag inputs coupled to the register bit flags.

15. The SoC of claim 13 in which the photoelectric amplifier circuit includes:
    a photo input amplifier having a first input coupled to a photodiode negative input terminal, having a second input coupled to a photodiode positive input terminal, and having a photo amplifier output coupled to a photodiode output terminal; and
    a photo gain amplifier having a first input coupled to the photo amplifier output and a photo gain output coupled to an analog sensor input.

16. The SoC of claim 1 in which the photoelectric amplifier circuit has a photodiode negative input terminal, has a photodiode positive input terminal, and has an output coupled to a sensor output terminal.

17. The SoC of claim 1 in which the carbon monoxide (CO) amplifier circuit includes an amplifier having an input coupled to a carbon monoxide negative terminal, an input coupled to a register bit flag, and an analog carbon monoxide amplifier output.

18. The SoC of claim 13 in which the carbon monoxide (CO) amplifier circuit includes an amplifier having an input coupled to a carbon monoxide negative terminal, an input coupled to a register bit flag, and an analog carbon monoxide amplifier output coupled to an analog sensor input.

19. The SoC of claim 1 in which the sensor amplifier circuits include an ionization amplifier circuit having an ion guard ring terminal, an ion in terminal, and an ionization amplifier output.

20. The SoC of claim 13 in which the sensor amplifier circuits include an ionization amplifier circuit having an ion guard ring terminal, an ion in terminal, and an ionization amplifier output coupled to an analog sensor input.

21. The SoC of claim 1 in which the light emitting driver circuit has an input coupled to a light emitting enable terminal, has an input coupled to a register bit flag, has a current sink terminal, and has a current sense terminal.

22. The SoC of claim 21 in which the light emitting driver circuit includes:
   gating having an input coupled to the light emitting enable terminal and having a gating output;
   an amplifier having an input coupled to the current sense terminal, having an input coupled to the gating output, having an input coupled to the register bit flags, and having an amplifier output; and
   a transistor having a control terminal coupled to the amplifier output and being coupled to the current sink terminal and to the current sense terminal.

23. The SoC of claim 1 in which the power regulator circuits include:
   a boost input terminal;
   a boost output terminal;
   an internal voltage terminal;
   an input voltage terminal;
   a pre-regulator terminal;
   an external voltage terminal; and
   a voltage selection terminal.

24. A smoke detection device comprising:
   (a) a system on a chip (SoC) that includes:
      power regulator circuits coupled to power regulator terminals,
      analog sensor amplifier circuits coupled to the power regulator terminals, the analog sensor amplifier circuits having a photoelectric amplifier circuit, a carbon monoxide amplifier circuit, and a light emitting diode driver circuit, and
      a digital core that includes a digital logic circuit, register bit flags, and a communication circuit, the communication circuit being coupled to a data terminal, the register bit flags being coupled to the power regulator circuits, the analog sensor amplifier circuits, and the the communication circuit;
   (b) sensors, each sensor of the sensors being coupled to a respective one of the analog sensor amplifier circuits;
   (c) a DC power supply coupled to the power regulator circuits; and
   (d) a microcontroller unit (MCU) chip that includes an upper power supply input, a digital processor, an analog to digital converter (ADC), an SoC communication circuit, and a general purpose I/O circuit, the upper power supply input on the MCU chip being coupled to receive power from the power regulator circuits.

25. The smoke detection device of claim 4 in which the register bit flags include status register bit flags and control register bit flags.

26. The smoke detection device of claim 4 in which the register bit flags include
   one of a sleep timer wakeup flag, a VCC low warning flag, an MCU LDO power good error flag, a thermal shutdown error flag, a thermal warning flag, a boost activity monitor flag, and a boost converter power good error flag.

27. The smoke detection device of claim 4 in which the register bit flags include register bit flag masks.

28. The smoke detection device of claim 27 in which the digital logic includes an interrupt signal alert logic circuit, the interrupt signal alert logic circuit including:
   a first interrupt AND gate having a first interrupt input coupled to a first register bit flag, a second interrupt input coupled to a first register bit flag mask, and a first interrupt output,
   a second interrupt AND gate having a first interrupt input coupled to a second flag, a second interrupt input coupled to a second register bit flag mask, and a second interrupt output, and
   an OR gate having inputs coupled to the first interrupt output and the second interrupt output and having an OR interrupt output coupled to an interrupt output terminal.

29. The smoke detection device as recited in claim 4 in which the communication circuit is an Inter-Integrated Circuit (I2C) interface coupled to a serial data terminal and having an input coupled to a serial clock terminal.

30. The smoke detection device as recited in claim 4 including an interconnect driver receiver circuit having an input coupled to a register bit flag and being coupled to an interconnect-to-MCU terminal and an interconnect-to-unit terminal.

31. The smoke detection device of claim 30 in which the interconnect driver receiver circuit includes:
   a hysteretic comparator having an input coupled to the interconnect-to-unit terminal and having a hysteretic output; and
   a deglitch circuit having an input coupled to the hysteretic output and having an output coupled to the interconnect-to-MCU terminal.

32. The smoke detection device of claim 4 including a signaling line circuit coupled to an signaling line receive terminal, a first signaling line transmit terminal, a second signaling line transmit terminal, an MCU receive terminal, a first MCU transmit terminal, and a second MCU transmit terminal.

33. The smoke detection device of claim 32 in which the signaling line circuit includes a comparator having an input coupled to the signaling line receive terminal and having an output coupled to the MCU receive terminal.

34. The smoke detection device of claim 32 in which the signaling line circuit includes:
   a first transmit amplifier circuit having an input coupled to the first MCU transmit terminal, having in input coupled to a transmit enable register bit flag, and having an output coupled to the first signaling line transmit terminal; and
   a second transmit amplifier circuit having an input coupled to the second MCU transmit terminal, having in input coupled to the transmit enable register bit flag, and having an output coupled to the second signaling line transmit terminal.

35. The smoke detection device of claim 4 including a horn driver circuit having a horn block enable input, having a feedback input coupled to a horn feedback terminal, having a first horn output coupled to a horn silver output terminal, and having a second horn output coupled to a horn brass output terminal.

36. The smoke detection device of claim 4 including an analog multiplexer circuit having analog sensor inputs coupled to the analog sensor amplifiers and having an analog multiplexer output coupled to an analog multiplexer output terminal.

37. The smoke detection device of claim 36 in which the analog sensor inputs include:
   an ION analog input;
   a carbon monoxide amplifier analog input;
   a photodiode output terminal input;
   a photo gain input; and
   register bit flag inputs coupled to the register bit flags.

38. The smoke detection device of claim 36 in which the photoelectric amplifier circuit includes:
   a photo input amplifier having a first input coupled to a photodiode negative input terminal, having a second input coupled to a photodiode positive input terminal, and having a photo amplifier output coupled to a photodiode output terminal; and
   a photo gain amplifier having a first input coupled to the photo amplifier output and a photo gain output coupled to an analog sensor input.

39. The smoke detection device of claim 4 in which the photoelectric amplifier circuit has a photodiode negative input terminal, has a photodiode positive input terminal, and has an output coupled to a sensor output terminal.

40. The smoke detection device of claim 4 in which the carbon monoxide (CO) amplifier circuit includes an amplifier having an input coupled to a carbon monoxide negative terminal, an input coupled to a register bit flag, and an analog carbon monoxide amplifier output.

41. The smoke detection device of claim 40 in which the carbon monoxide (CO) amplifier circuit includes an amplifier having an input coupled to a carbon monoxide negative terminal, an input coupled to a register bit flag, and an analog carbon monoxide amplifier output coupled to an analog sensor input.

42. The smoke detection device of claim 4 in which the sensor amplifier circuits include an ionization amplifier circuit having an ion guard ring terminal, an ion in terminal, and an ionization amplifier output.

43. The smoke detection device of claim 36 in which the sensor amplifier circuits include an ionization amplifier circuit having an ion guard ring terminal, an ion in terminal, and an ionization amplifier output coupled to an analog sensor input.

44. The smoke detection device of claim 4 in which the light emitting driver circuit has an input coupled to a light emitting enable terminal, has an input coupled to a register bit flag, has a current sink terminal, and has a current sense terminal.

45. The smoke detection device of claim 44 in which the light emitting driver circuit includes:
   gating having an input coupled to the light emitting enable terminal and having a gating output;
   an amplifier having an input coupled to the current sense terminal, having an input coupled to the gating output, having an input coupled to the register bit flags, and having an amplifier output; and
   a transistor having a control terminal coupled to the amplifier output and being coupled to the current sink terminal and to the current sense terminal.

46. The smoke detection device of claim 4 in which the power regulator circuits include:
   a boost input terminal;
   a boost output terminal;
   an internal voltage terminal;
   an input voltage terminal;
   a pre-regulator terminal;
   an external voltage terminal; and
   a voltage selection terminal.

47. An integrated circuit comprising:
   (a) power regulator circuits having DC/DC boost terminals, a pre-low drop out terminal, an internal voltage terminal, and a controller voltage terminal;
   (b) carbon monoxide amplifier circuits having carbon monoxide sensor terminals and a carbon monoxide amplifier output;
   (c) photoelectric circuits having positive and negative photoelectric terminals, a photodiode out terminal, and a photodiode amplifier output;
   (d) ionization amplifier circuits having ionization terminals and having an ionization amplifier output;
   (e) analog multiplexer circuits having a first input coupled to the carbon monoxide amplifier output, having a second input coupled to the photodiode out terminal, a third input coupled to the photodiode amplifier output, selector inputs, and an analog output coupled to a sensor output terminal;
   (f) horn driver circuits having horn terminals and a horn control input;
   (g) interconnect buffer circuits having a controller communication terminal and having a system communication terminal; and
   (h) digital core circuits having:
      controller terminals;
      register bit flags coupled to the controller terminals, to the power regulator circuits, to the carbon monoxide amplifier circuits, to the photoelectric circuits, to the ionization amplifier circuits, to the analog multiplexer circuits selector inputs, to the horn driver circuits, and to the interconnect buffer circuits;
      interface circuits coupled between the controller terminals and the register bit flags; and
      interrupt circuits having inputs coupled to the register bit flags and an output coupled to the controller terminals.

48. The integrated circuit of claim 47 including power circuits off of the integrated circuit coupled to the power regulator terminals.

49. The integrated circuit of claim 47 including carbon monoxide sensor circuits off of the integrated circuit coupled to the carbon monoxide amplifier circuits.

50. The integrated circuit of claim 47 including photo sensor circuits off of the integrated circuit coupled to the photoelectric terminals.

51. The integrated circuit of claim 47 including light emitting diode circuits off of the integrated circuit coupled to the photoelectric terminals.

52. The integrated circuit of claim 47 including ionization sensor circuits off of the integrated circuit coupled to the ionization terminals.

53. The integrated circuit of claim 47 including horn circuits off of the integrated circuit coupled to the horn terminals.

54. The integrated circuit of claim 47 including microcontroller circuits off of the integrated circuit coupled to the controller terminals, the controller communication terminal, the sensor output terminal, and the controller voltage terminal.

* * * * *